US012788294B2

(12) United States Patent
Galeev et al.

(10) Patent No.: US 12,788,294 B2
(45) Date of Patent: Nov. 10, 2026

(54) FATIGUE EVALUATION BASED ON SLEEP QUALITY AND PHYSICAL ACTIVITY

(71) Applicants: Zepp, Inc., Cupertino, CA (US); Anhui Huami Health Technology Co., Ltd., Hefei (CN)

(72) Inventors: Artem Galeev, Vancouver (CA); Di Feng, Shanghai (CN); Shuai Huang, Shanghai (CN); Yan Vule, Port Moody (CA); Kongqiao Wang, Hefei (CN)

(73) Assignees: Zepp, Inc., Milpitas, CA (US); Anhui Huami Health Technology Co., Ltd., Hefei (CN)

( * ) Notice: Subject to any disclaimer, the term of this patent is extended or adjusted under 35 U.S.C. 154(b) by 545 days.

(21) Appl. No.: 17/990,210

(22) Filed: Nov. 18, 2022

(65) Prior Publication Data

US 2024/0164678 A1 May 23, 2024

(51) Int. Cl.
*A61B 5/18* (2006.01)
*A61B 5/00* (2006.01)
*A61B 5/11* (2006.01)

(52) U.S. Cl.
CPC .............. *A61B 5/18* (2013.01); *A61B 5/1118* (2013.01); *A61B 5/4809* (2013.01); *A61B 5/4815* (2013.01); *A61B 5/4857* (2013.01); *A61B 5/746* (2013.01)

(58) Field of Classification Search
CPC ....... A61B 5/18; A61B 5/1118; A61B 5/4809; A61B 5/4815; A61B 5/4857; A61B 5/746
See application file for complete search history.

(56) References Cited

U.S. PATENT DOCUMENTS

| | | | |
|---|---|---|---|
| 7,898,426 | B2 | 3/2011 | Rai et al. |
| 8,948,861 | B2 | 2/2015 | Rai et al. |
| 9,770,444 | B2 | 9/2017 | Eichele et al. |
| 2003/0013943 | A1 | 1/2003 | Hursh |

(Continued)

FOREIGN PATENT DOCUMENTS

WO WO-2021235333 A1 * 11/2021

OTHER PUBLICATIONS

Kitamura et al.; Estimating Individual Optimal Sleep Duration and Potential Sleep Debt; Scientific Reports; pp. 1-9; Mar. 9, 2016.
Robert Refinetti; Circadian Rhythmicity of Body Temperature and Metabolism; ISSN: (Print) (Online) Journal homepage: https://www.tandfonline.com/loi/ktmp20; Apr. 17, 2020, vol. 7, No. 4, pp. 321-362.

(Continued)

*Primary Examiner* — Amanda L Steinberg
*Assistant Examiner* — Laura Hodge
(74) *Attorney, Agent, or Firm* — Young Basile Hanlon & MacFarlane, P.C.

(57) ABSTRACT

A circadian rhythm (CR) oscillator is obtained for a person based at least in part on a bathyphase time. A fatigue value is calculated for the person. Calculating the fatigue value includes, in response to determining that the person is in sleep, subtracting a sleep recovery unit from the fatigue value in a time unit; and accumulating, in a first time range of the sleep, a total sleep inertia by an inertia in sleep in the time unit. The sleep recovery unit is calculated based on the CR oscillator and a recovery debt In response to determining that the person is performing an activity and determining that the fatigue value is above a threshold, the person is notified to recover to decrease the fatigue value below the threshold prior to performing the activity.

20 Claims, 10 Drawing Sheets

(56) References Cited

U.S. PATENT DOCUMENTS

| | | | | |
|---|---|---|---|---|
| 2006/0142646 | A1 | 6/2006 | Hursh et al. | |
| 2008/0132798 | A1* | 6/2008 | Hong | A61B 5/0002 600/508 |
| 2009/0134819 | A1* | 5/2009 | Noguchi | A61B 5/4809 600/27 |
| 2016/0374567 | A1* | 12/2016 | Breslow | A61B 5/02405 600/301 |
| 2017/0000399 | A1* | 1/2017 | Lore | A61B 5/18 |
| 2018/0206749 | A1* | 7/2018 | Chen | A61B 5/347 |
| 2021/0169417 | A1* | 6/2021 | Burton | A61B 5/4857 |
| 2021/0290961 | A1* | 9/2021 | Greenberg | A61N 1/3611 |
| 2022/0096007 | A1* | 3/2022 | Robinson | G16H 40/63 |
| 2022/0273232 | A1* | 9/2022 | Capodilupo | G16H 40/67 |

OTHER PUBLICATIONS

W.P. Colquhoun et al.; Circadian Rhythms of Body Temperature in Shift-Workers at a Coalface; Brit. J. Industr. Med., Medical Research Council, Applied Psychology Unit, Cambridge; 1970, pp. 266-272.

Benjamin Coiffard et al.; A Tangled Threesome: Circadian Rhythm, Body Temperature Variations, and the Immune System; Biology 2021, 10, 65, https//doi/org/10.3390/biology10010065; pp. 1-16.

Soo Young Sim et al.; Estimation of Circadian Body Temperature Rhythm Based on Heart Rate in Healthy, Ambulatory Subjects; IEEE Journal of Biomedical and Health Informatics, vol. 21, No. 2, Mar. 2017; pp. 407-415.

Cassie J. Hilditch, Phd et al.; A Review of Short Naps and Sleep Inertia: Do Naps of 30 Min or Less Really Avoid Sleep Inertia and Slow Wave Sleep; 2017; Sleep Medicine, vol. 32; pp. 176-190.

* cited by examiner

FATIGUE EVALUATION BASED ON SLEEP QUALITY AND PHYSICAL ACTIVITY

FIELD

The present disclosure relates to fatigue assessment.

SUMMARY

A first aspect is a method that includes obtaining a circadian rhythm (CR) oscillator for a person based at least in part on a bathyphase time; calculating a fatigue value for the person; and, in response to determining that the person is performing an activity and determining that the fatigue value is above a threshold, notifying the person to recover to decrease the fatigue value below the threshold prior to performing the activity. Calculating the fatigue value for the person includes, in response to determining that the person is in sleep, subtracting a sleep recovery unit from the fatigue value in a time unit; and accumulating, in a first time range of the sleep, a total sleep inertia by an inertia in sleep in the time unit. The sleep recovery unit is calculated based on the CR oscillator and a recovery debt.

A second aspect is a device that includes a process that is configured to obtain a circadian rhythm (CR) oscillator for a person based at least in part on a bathyphase time; calculate a fatigue value for the person; and, in response to determining that the person is performing an activity and determining that the fatigue value is above a threshold, notify the person to recover to decrease the fatigue value below the threshold prior to performing the activity. To calculate the fatigue value for the person includes to, in response to determining that the person is in sleep, subtract a sleep recovery unit from the fatigue value in a time unit; and accumulate, in a first time range of the sleep, a total sleep inertia by an inertia in sleep in the time unit. The sleep recovery unit is calculated based on the CR oscillator and a recovery debt.

A third aspect is a non-transitory computer readable medium that stores instructions operable to cause one or more processors to perform operations that include obtaining a circadian rhythm (CR) oscillator for a person based at least in part on a bathyphase time; calculating a fatigue value for the person; and, in response to determining that the person is performing an activity and determining that the fatigue value is above a threshold, notifying the person to recover to decrease the fatigue value below the threshold prior to performing the activity. Calculating the fatigue value for the person includes, in response to determining that the person is in sleep, subtracting a sleep recovery unit from the fatigue value in a time unit; and accumulating, in a first time range of the sleep, a total sleep inertia by an inertia in sleep in the time unit. The sleep recovery unit is calculated based on the CR oscillator and a recovery debt.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
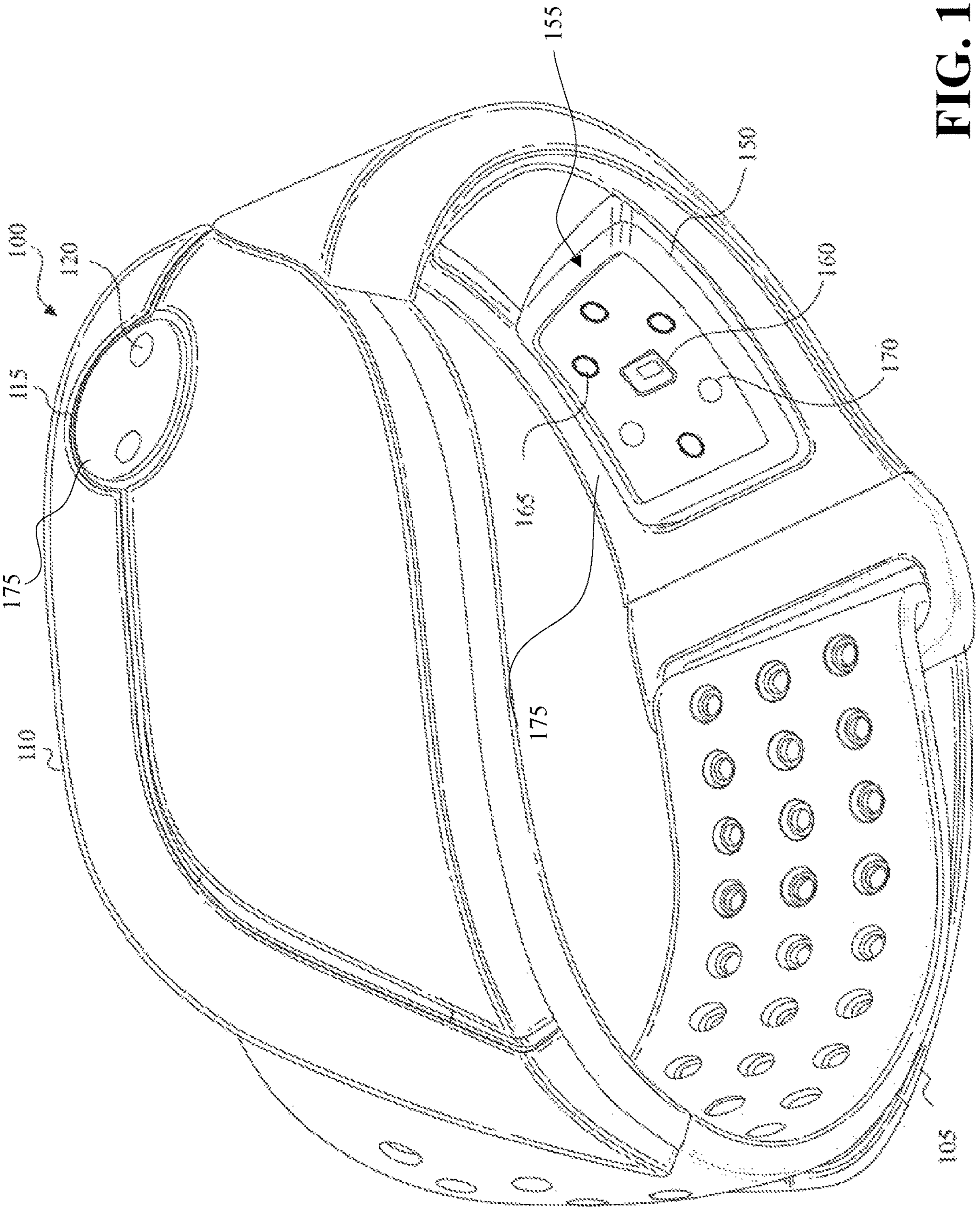
FIG. 1 depicts a perspective view of a device that is according to the teachings herein.

Fatigue is of high concern, especially to human health. Fatigue is known to slow down reaction times, reduce attention or concentration, limit short-term memory, and impair judgement. There are different types of fatigue including social fatigue, emotional fatigue, physical fatigue, mental fatigue, and chronic illness fatigue. Causes of fatigue may include physical or mental overwork, inadequate rest time, sleep deprivation, and circadian rhythm disruption, to name a few. Circadian rhythm disruption may result in poor performance, and even disability, in carrying out work activities and daily tasks. Fatigue may cause or result in depression, tiredness, lack of motivation, irritability, errors in performing tasks (potentially resulting in accidents), slowing down reaction times, reducing attention or concentration, limiting short-term memory, impairing judgement, and other negative consequences.

Real-time, continuous monitoring, evaluation, or prediction of the fatigue level of a person can be used to, for example, identify for a person that his/her fatigue level may be too high to undertake certain activities (such as current, anticipated, or planned activities) or that rest is required to increase work capacity or improve the person's quality of life.

A wearable device that includes one or more sensors and a data collector can be attached to or worn by a person to collect heart rate (HR) data, sleep (and wakefulness) data, physical exercise data, other data, or a combination thereof to evaluate physical and mental fatigue based on a fatigue model, as described herein.

According to implementations of this disclosure, fatigue level (FG) (which may also be referred to herein as fatigue amount, or, simply, fatigue) of a person can be determined starting with a circadian rhythm (CR) oscillator model (or, simply, a CR oscillator) that depicts a person's physical, mental, and behavioral changes that follow a time cycle (e.g., a 24 hour cycle), for example, which may be obtained based on or correlated to a temperature of a human body throughout a day. The CR oscillator can be approximated using at least one of acrophase or bathyphase of the body. The CR oscillator can then be adjusted based on characteristics of the person (e.g., the person's age group, lifestyle, or both).

Based on the CR oscillator, the FG can be calculated during sleep and wakefulness periods. During sleep, the FG can be dynamically updated by reducing a recovery in sleep (RS). RS refers to an amount by which accumulated fatigue is reduced because of, for example, rest attained during sleep. The CR oscillator, an individual sleep need (IS), and a recovery debt (RD) can be used to calculate the RS at regular intervals (e.g., every minute). IS refers to an amount of sleep per day that allows a person's body and mind to, for example, recharge (i.e., reduce the fatigue level). To illustrate, school-age children (e.g., ages 6-13) need 9-11 hours a day. RD refers to an amount of needed recovery time for a person's accumulated fatigue. The fatigue recovery in sleep may be affected by sleep quality which may be in turn be affected by fragmentation (FRG) and excess heart rate (ER). FRG is a number of uninterrupted wakefulness periods during sleep. ER refers to an excess of the previous night's sleep heart rate over a median sleep heart rate during consecutive nights. The FRG and the ER can be used to calculate a sleep recovery (SREC) and an adjusted sleep recovery ($SREC_a$), the difference of which (i.e., SREC-$SREC_a$) can be added to the FG. Likewise, an accumulated sleep inertia (SLIa) can be also added to the FG. SREC refers to an amount of recovery for fatigue during sleep. $SREC_a$ refers to an adjusted SREC in terms of sleep quality. SLIa refers to a fatigue value accumulated by sleep inertia during transitional time between sleep and wakefulness.

During wakefulness, FG may be accumulated, such as due to physical or mental activities. In an example, FG can be accumulated by a constant value (Fd) indicative of continuous increase of the fatigue at regular intervals (e.g., every minute). As fatigue increases during wakefulness periods, a total of physical fatigue (AF) can be added to the FG. A cognitive fatigue (CF) is calculated in terms of the FG, the CR oscillator, and the SLIa. In an example, at least one of the calculated physical fatigue (AF) or cognitive fatigue (CF) can be used to warn the person whose fatigue level is being monitored (also referred to as a user or the person wearing the device) of currently understanding or undertaking certain activities in the future. For example, if a person has a high FG, the person may be advised to take some rest prior to undertaking certain activities (e.g., driving for long distances or high traffic environment or complicated work assignments). Implementations according to this disclosure can identify for the person the minimal amount of rest required prior to undertaking a certain activity or continuing with a current activity. For example, if the FG is low for the person, the person may undertake physical exercise and heavy work.

It should be noted that the applications and implementations of this disclosure are not limited to the examples, and alternations, variations, or modifications of the implementations of this disclosure can be achieved for any computation environment. Details of the disclosed methods, apparatus, and systems will be set forth below after an overview of the system and coding structures.

FIG. 1 depicts a perspective view of a device 100 that is according to the teachings herein. The device 100 may be a physiological monitor worn by a user to at least one of sense, collect, monitor, analyze, or display information pertaining to one or more physiological characteristics to provide physiological information. The device 100 comprises a band, strap, or wristwatch. The device 100 is a wearable monitoring device configured for positioning at a user's wrist, arm, another extremity of the user, or some other area of the user's body.

The device 100 may comprise at least one of an upper module 110 or a lower module 150, each comprising at least one of one or more sensing tools including sensors and processing tools for detecting, collecting, processing, or displaying one or more physiological parameters and/or physiological characteristics of a user and/or other information that may or may not be related to health, wellness, exercise, sleep, or physical training sessions (e.g., characteristic information).

The upper module 110 and the lower module 150 of the device 100 may comprise a strap or band 105 extending from opposite edges of each module for securing device 100 to the user. The band(s) 105 may comprise an elastomeric material or the band(s) 105 may comprise some other suitable material, including but not limited to, a fabric or metal material.

Upper module 110 or lower module 150 may also comprise a display unit (not shown) for communicating information to the user (i.e., the wearer of the device). The display unit may be an LED indicator comprising a plurality of LEDs, each a different color. The LED indicator can be configured to illuminate in different colors depending on the information being conveyed. For example, where device 100 is configured to monitor at least one of the user's heart rate or respiration rate, the display unit may illuminate light of a first color when at least one of the user's hear rate or respiration rate is in a first numerical range, illuminate light of a second color when at least one of the user's hear rate or respiration rate is in a second numerical range, and illuminate light of a third color when at least one of the user's hear rate or respiration rate is in a third numerical range. In this manner, a user may be able to detect his or her approximate heart rate and/or respiration rate at a glance, even when numerical heart rate information and/or respiration rate information is not displayed at the display unit, and/or the user only sees device 100 through the user's peripheral vision.

The display unit may comprise a display screen for displaying images, characters, graphs, waveforms, or a combination thereof to at least one of the user or a medical professional. The display unit may further comprise one or more hard or soft buttons or switches configured to accept input by the user. The display unit may switch or be toggled between displaying user physiological information.

The device 100 may further comprise one or more communication modules. Each of the upper module 110 and the lower module 150 may comprise a communication module such that information received at either module can be shared with the other module. One or more communication modules may also communicate with other devices such as personal device of the user (such as a handheld device, a smart phone, a tablet, a laptop computer, a desktop computer, or the like) or a server (such as a cloud-based server). The communications between the upper and lower modules can be transmitted from one module to the other wirelessly (e.g., via Bluetooth, RF signal, Wi-Fi, near field communications, etc.) or through one or more electrical connections embedded in band 105. Any analog information collected or analyzed by either module can be translated to digital information for reducing the size of information transfers between modules. Similarly, communications between either module and device can be transmitted wirelessly or through a wired connection, and translated from analog to digital information to reduce the size of data transmissions.

As shown in FIG. 1, lower module 150 can comprise an array of sensor array 155 including but not limited to one or more optical detectors 160, one or more light sources 165, one or more contact pressure/tonometry sensors 170, and at least one of the one or more gyroscopes or accelerometers 175. These sensors are only illustrative of the possibilities, however, and lower module may comprise additional or alternative sensors such as one or more acoustic sensors, electromagnetic sensors, ECG electrodes, bio impedance sensors, or galvanic skin response, or a combination thereof. Though not depicted in the view shown in FIG. 1, upper module 110 may also comprise one or more such sensors and components on its inside surface, i.e., the surface in contact with the user's tissue or targeted area.

The location of sensor array 155 or the location of one or more sensor components of sensor array 155 with respect to the user's tissue may be customized to account for differences in body type across a group of users or placement in different locations on a user. For example, band 105 may comprise an aperture or channel within which lower module 150 is movably retained. In one implementation, lower module 150 and channel can be configured to allow lower module 150 to slide along the length of channel using, for example, a ridge and groove interface between the two components. For example, if the user desires to place one more components of sensor array 155 at a particular location on his or her wrist, or mid-section, the lower module 150 can be slid into the desired location along band 105. Though not depicted in FIG. 1, band 105 and upper module 110 can be similarly configured to allow for flexible or customized placement of one or more sensor components of upper module 110 with respect to the user's wrist or targeted tissue area.

The sensors and components proximate or in contact with the at least one of the user's tissue, upper module 110, or lower module 150 may comprise additional sensors or components on their respective outer surfaces, i.e., the surfaces facing outward or away from the user's tissue. In the implementation depicted in FIG. 1, upper module 110 comprises one such outward facing sensor array 115. The sensor array 115 may comprise one or more ECG electrodes 120, and/or one or more gyroscopes and/or accelerometers 175. Similar to the sensor arrays of the upper and lower modules proximate or in contact with the user's tissue, outward facing sensor array 115 may further comprise one or more contact pressure/tonometry sensors, photo detectors, light sources, acoustic sensors, electromagnetic sensors, bio impedance sensors, accelerometer, gyroscope, and/or galvanic skin response sensors.

The outward facing sensors of sensor array 115 can be configured for activation when touched by the user (with his or her other hand) and used to collect additional information. The outward facing sensors may measure without being in direct contact with the user. The outward facing sensors of sensor array 115 may be an accelerometer 175 and the accelerometer 175 may indirectly monitor movements or micro-movements (e.g., an acceleration or a velocity change) that are transmitted to the sensor through the band or the module moving or being moved or a gyroscope that monitors velocities to determine micro-movements. In an example, where lower module 150 comprises one or more optical detectors 160 and light sources 165 for collecting ECG, PPG, or heart rate information of the user, outward facing sensor array 115 of upper module 110 may comprise ECG electrodes 120 that can be activated when the user places a fingertip in contact with the electrodes. While the optical detectors 160 and light sources 165 of lower module 150 can be used to continuously monitor blood flow of the user, outward facing sensor array 115 of upper module 110 can be used periodically or intermittently to collect potentially more accurate blood flow information which can be used to supplement or calibrate the measurements collected and analyzed by an inward facing sensor array, the sensor array 155, of lower module 150.

In addition to the inward and outward facing sensors, device 100 may further comprise additional internal components such at least one of the as one or more accelerometers or gyroscopic components for determining whether and to what extent the user is in motion (i.e., whether the user is walking, jogging, running, swimming, sitting, or sleeping), breathing rhythm, breathing signals, or a combination thereof of a user. Information collected by at least one of the accelerometer(s) or gyroscopic components can also be used to calculate the number of steps a user has taken over a period of time. The activity information may measure movements. The movements measured may be macro-movements such as walking or jogging. The movements may be micro-movements.

The micro-movements may be caused by a surface of a user's skin or body part being moved due to respiration, heartbeat, or a both. The micro-movements may have a displacement (e.g., length) less than a predetermined displacement in order for at least one of the accelerometer or gyroscope to at least one of the measure or record the micro-movements. For example, when a user walks the accelerometer may measure a movement of more than 1 cm, when the accelerometer detects a user heart beat the accelerometer may measure a displacement of between 4 mm and 1 cm, and when the accelerometer measures a displacement of 4 mm or less (e.g., a micro-movement). The micro-movements may be charted in wave form such that the micro-movements are charted with a peak and a valley.

The displacement values may assist a non-transitory computer readable medium or processor in isolating movements caused by multiple sources (e.g., heart beat and respiration). The processor may receive data from at least one of the accelerometer or gyroscope related to movements of the user. The processor may dynamically filter the data. The processor may provide a respiratory signal regarding the respiration of the user (referred to herein also as acceleration data). The processor may analyze the acceleration data without regard to a position of the device relative to the user or a position of the user. The processor may filter out unwanted signals and isolate only desired signals. For example, the processor may learn which signals are of interest and the processor may analyze only those signals of interest. The processor may be in communication with or include a non-transitory computer-readable medium.

At least one of the upper or lower modules 110 or 150 can be configured to continuously collect data from a user using an inward facing sensor array. However, certain techniques can be employed to reduce power consumption and conserve battery life of device 100. For instance, only one of the upper or lower modules 110 or 150 may continuously collect information. The module may be continuously active, but may wait to collect information when conditions are such that accurate readings are most likely.

For example, when one or more accelerometers or gyroscopic components of device 100 indicate that a user is still, at rest, or sleeping, one or more sensors of at least one of the upper module 110 or lower module 150 may collect information from the user while artifacts resulting from physical movement are absent. The accelerometer or gyroscope may not begin reading until the heart rate of the user measured by another sensor is below a predetermined limit. For example, if the ECG or PPG demonstrates that the user is moving then, the accelerometer or gyroscope may not be turned on. In another example, the accelerometer or gyroscope may turn off if macro-movements are detected or a number of macro-movements are detected above a threshold amount (e.g., 5 or more per min, 10 or more per min, 20 or more per min, 30 or more per min, or 60 or more per minute). The processor may be configured to remove or filter out macro-movements. Thus, the accelerometer or gyroscope may only measure micro-movements if the macro-movements are below the threshold amount (e.g., 20 or less per minute, 10 or less per minute, 5 or less per minute, or 2 or less per minute). Thus, the accelerometer or gyroscope when set, placed, or configured to read micro-movements may only be activated when macro-movements are not present or when macro-movements are infrequent. The accelerometer or gyroscope may measure micro-movements and macro-movements simultaneously and the macro-movements may be considered outliers and may be removed from reporting. Data provided by at least one of the accelerometer or gyroscope may include an x-component, a y-component, a z-component, or a combination of the x/y/z-components within a coordinate system.

The physiological information from an upper module 110, a lower module 150, or both may be graphically displayed or represented by a waveform on a display (not shown) of the device 100. The graphical display may be provided as an output. The output may include physiological information of a user. For example, the information collected may be categorized and then graphically represented as an output or two or more outputs. The one or more outputs may be one or more waveforms, two or more waveforms, or three or more waveforms. The waveforms may be individually created. The waveforms may overlay one another. The waveforms may be created by categorizing the micro-movements. The micro-movements may be categorized by strength of the micro-movements, frequency of the micro-movements, duration of the micro-movements, or a combination thereof. The waveforms may be a one or more waveforms such as a sine wave or a sinusoidal pattern. The output may have one graph having respiration signals and a graph having a heart rate.

Figure 2:
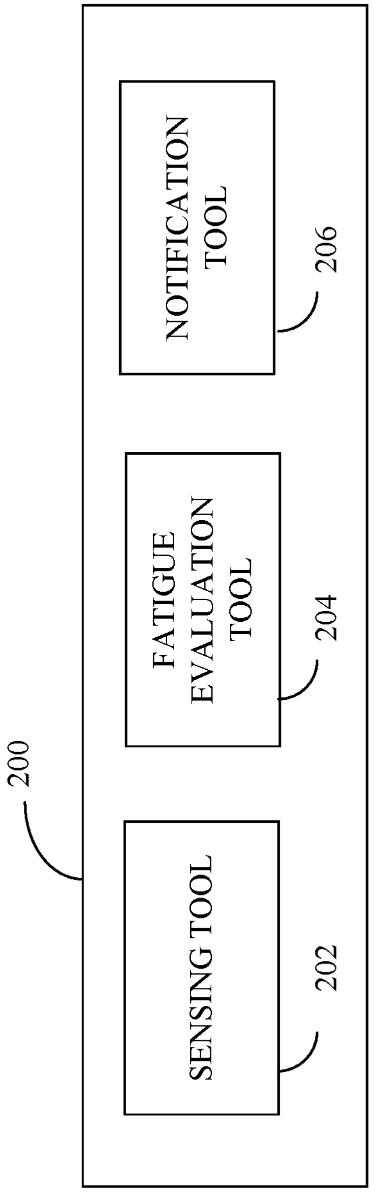
FIG. 2 depicts a system for fatigue assessment.

FIG. 2 depicts a system 200 for fatigue assessment. The system 200 includes tools, such as programs, subprograms, functions, routines, subroutines, operations, executable instructions, specialized hardware, and/or the like for, inter alia and as further described below, fatigue assessment. As shown, the system 200 implements or includes a sensing tool 202, a fatigue evaluation tool 204, and a notification tool 206. In some implementations, some of the tools may be combined, some of the tools may be split into more tools, or a combination thereof.

The tools of the system 200 may be differently configured or included in different devices. In an example, the tools 202-206 may be implemented or included in a single device, such as a wearable device that can be the device 100 of FIG. 1. In an example, the sensing tool 202 may be implemented or included in a wearable device that is in communication with another device that implements or includes the fatigue evaluation tool 204 and the notification tool 206. The other device can be a hand-held device, a tablet, a desktop device, a network-based server (e.g., a cloud-based server), or the like. In an example, the sensing and fatigue evaluation tools 202-204 may be implemented or included in a wearable device and at the notification tool 206 may be implemented or included in another device. In an example, the sensing tool 202 may be implemented or included in a wearable device and the fatigue evaluation and notification tools 204-206 may be implemented or included one or more other devices. In an example, the sensing tool 202 may be included in a wearable device that is in communication with a personal device, which includes the fatigue evaluation tool 204 and the notification tool 206. Other configurations of the tools 202-206 are possible.

Devices (e.g., one or more of a wearable device, a personal device, and a server) implementing or including the tools 202-206 can communicate via wired or wireless connections. A wired connection can be a Universal Serial Bus (USB) connection, a firewire connection, or the like. A wireless connection can be via a network using Bluetooth communications, infrared communications, near-field communications (NFCs), a cellular data network, or an Internet Protocol (IP) network.

The sensing tool 202 can include or be a sensing unit. The sensing unit can include an accelerometer (e.g., a 3D accelerometer). The sensing unit may include other sensors, as described with respect to FIG. 1. As such, the sensing unit may include a pulse oximeter, an electrocardiogram, an optical sensor, an acoustical sensor or other sensors. At least one of the sensors may be a heart rate sensor that is used to monitor heart rate. As already mentioned, the sensing tool 202 and sensing unit are included in a wearable device that is worn on the body during sleep. In an example, the device can be a wrist watch, such as the device 100 of FIG. 1. In an example, the optical sensor, the acoustical sensor, or both can be used as the heart rate sensor. As such, the sensing tool 202 can be used to configure the optical sensor and the acoustical sensor for heart rate monitoring. The sensing tool 202 can determine (e.g., obtain or calculate) data related to sleep (such as whether a person is asleep or awake, the number of periods of uninterrupted sleep), heart rate data, and other data described herein to evaluate asleep. For example, the acoustical sensor in FIG. 3 can be enabled to generate an acoustical sensor signal corresponding to heart rate that can be used to check whether a person is asleep or awake. The data may be received from sensors at least as described with respect to FIGS. 1 and 3.

For example, the sensing tool 202 can be used to configure a sensitivity of the acoustical sensor, to turn on or off the acoustical sensor, and the like. The acoustical sensor may be configured by a user (such as the wearer of the wearable device) or automatically configured to collect heart rate data. In an example, in response to other tools of the wearable device detecting that the user is attempting to go to sleep (such as by detecting a body position, a breathing rate, an absence of macro-movements, or some other conditions), the acoustical sensor can be enabled to generate an acoustical sensor signal corresponding to heart rate. Regardless of how the acoustical sensor is enabled, the sensing tool 202 detects or obtains acoustical sensor signals associated with heart rate, as described herein.

The sensing tool 202 can receive signals detected by the acoustical sensor and transmit the acoustical sensor signals to the fatigue evaluation tool 204. In an example, the acoustical sensor signals may be analog signals. Depending on the configuration of the system 200, the acoustical sensor signal may be transmitted to the fatigue evaluation tool 204 via wired communication, wireless communication, or via some other communication mechanism known to a person skilled in the art.

The fatigue evaluation tool 204 receives the acoustical sensor signals from the sensing tool 202 and outputs (e.g., determines, calculates, or infers) fatigue values of physical fatigue and cognitive fatigue. In an example, the fatigue evaluation tool 204 can output respective labels for ranges of the physical fatigue value and the cognitive fatigue value.

The notification tool 206 can be used to notify a remote server or a user to store and analyze historical heart rate data, the corresponding outputs of the fatigue evaluation tool 204, or both to provide historical insights, suggestions/recommendations, etc.

Figure 3:
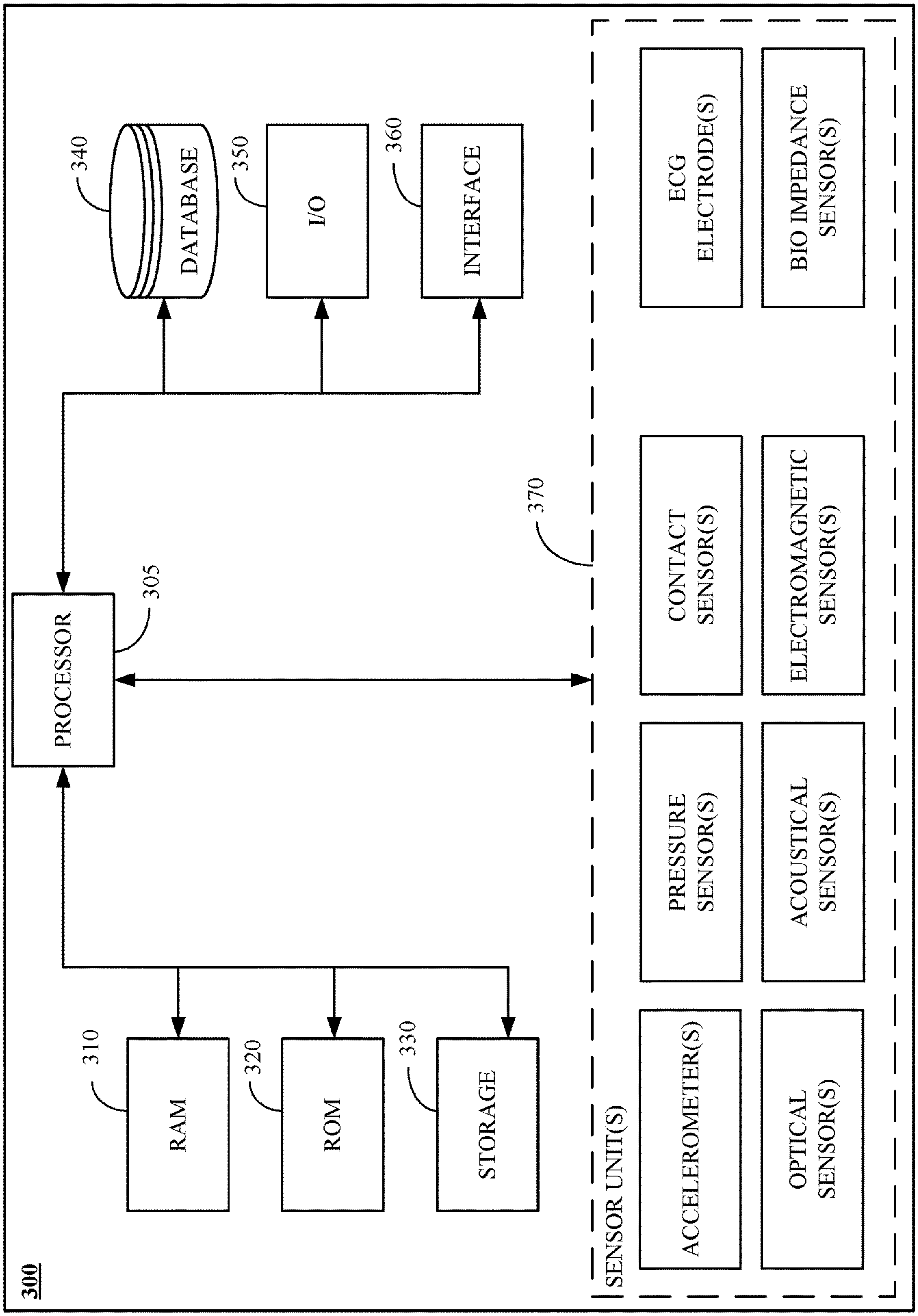
FIG. 3 depicts an illustrative processor-based computing device.

FIG. 3 depicts an illustrative processor-based computing device 300. The computing device 300 is representative of the type of computing device that may be present in or used in conjunction with at least some aspects of device 100 or devices implementing the tools of FIG. 2, or any other device comprising electronic circuitry. For example, the computing device 300 may be used in conjunction with any one or more of transmitting signals to and from the one or more optical sensors or acoustical sensors, sensing or detecting signals received by one or more sensors of device 100, processing received signals from one or more components or modules of device 100 or a secondary device, and storing, transmitting, or displaying information. The computing device 300 is illustrative only and does not exclude the possibility of another processor- or controller-based system being used in or with any of the aforementioned aspects of device 100. At least some aspects of the computing device 300 may be included, but others may not be or may not be used to implement tools described with respect to FIG. 2, in a device that works in conjunction with the device 100 of FIG. 1 to implement the system 200 of FIG. 2. For example, a user device or a server may or may not include one or more sensor modules 370.

In one aspect, the computing device 300 may include one or more hardware and/or software components configured to execute software programs, such as software for obtaining, storing, processing, and analyzing signals, data, or both. For example, the computing device 300 may include one or more hardware components such as, for example, a processor 305, a random-access memory (RAM) 310, a read-only memory (ROM) 320, a storage 330, a database 340, one or more input/output (I/O) modules 350, an interface 360, and the one or more sensor modules 370. Alternatively and/or additionally, the computing device 300 may include one or more software components such as, for example, a computer-readable medium including computer-executable instructions for performing techniques or implement functions of tools consistent with certain disclosed embodiments. It is contemplated that one or more of the hardware components listed above may be implemented using software. For example, the storage 330 may include a software partition associated with one or more other hardware components of the computing device 300. The computing device 300 may include additional, fewer, and/or different components than those listed above. It is understood that the components listed above are illustrative only and not intended to be limiting or exclude suitable alternatives or additional components.

The processor 305 may include one or more processors, each configured to execute instructions and process data to perform one or more functions associated with the computing device 300. The term "processor," as generally used herein, refers to any logic processing unit, such as one or more central processing units (CPUs), digital signal processors (DSPs), application specific integrated circuits (ASICs), field programmable gate arrays (FPGAs), and similar devices. As illustrated in FIG. 3, the processor 305 may be communicatively coupled to the RAM 310, the ROM 320, the storage 330, the database 340, the I/O module 350, the interface 360, and the one or more sensor modules 370. The processor 305 may be configured to execute sequences of computer program instructions to perform various processes, which will be described in detail below. The computer program instructions may be loaded into the RAM 310 for execution by the processor 305.

The RAM 310 and the ROM 320 may each include one or more devices for storing information associated with an operation of the computing device 300 and/or the processor 305. For example, the ROM 320 may include a memory device configured to access and store information associated with the computing device 300, including information for identifying, initializing, and monitoring the operation of one or more components and subsystems of the computing device 300. The RAM 310 may include a memory device for storing data associated with one or more operations of the processor 305. For example, the ROM 320 may load instructions into the RAM 310 for execution by the processor 305.

The storage 330 may include any type of storage device configured to store information that the processor 305 may use to perform processes consistent with the disclosed embodiments.

The database 340 may include one or more software and/or hardware components that cooperate to store, organize, sort, filter, and/or arrange data used by the computing device 300 and/or the processor 305. For example, the database 340 may include user profile information, historical activity and user-specific information, physiological parameter information, predetermined menu/display options, and other user preferences. Alternatively, the database 340 may store additional and/or different information. The database 340 can be used to store fatigue values, features extracted therefrom, outputs of the fatigue evaluation tool 204 of FIG. 2, other data used or generated by the system 200 of FIG. 2, or a combination thereof.

The I/O module 350 may include one or more components configured to communicate information with a user associated with the computing device 300. For example, the I/O module 350 may comprise one or more buttons, switches, or touchscreens to allow a user to input parameters associated with the computing device 300. The I/O module 350 may also include a display including a graphical user interface (GUI) and/or one or more light sources for outputting information to the user. The I/O module 350 may also include one or more communication channels for connecting the computing device 300 to one or more secondary or peripheral devices such as, for example, a desktop computer, a laptop, a tablet, a smart phone, a flash drive, or a printer, to allow a user to input data to or output data from the computing device 300.

The Interface 360 may include one or more components configured to transmit and receive data via a communication network, such as the Internet, a local area network, a workstation peer-to-peer network, a direct link network, a wireless network, or any other suitable communication channel. For example, the interface 360 may include one or more modulators, demodulators, multiplexers, demultiplexers, network communication devices, wireless devices, antennas, modems, and any other type of device configured to enable data communication via a communication network.

The computing device 300 may further comprise the one or more sensor modules 370. In one embodiment, the one or more sensor modules 370 may comprise one or more of an accelerometer module, an optical sensor module, an acoustical sensor module, and/or an ambient light sensor module. Of course, these sensors are only illustrative of a few possibilities and the one or more sensor modules 370 may comprise alternative or additional sensor modules suitable for use in the device 100. It should be noted that although one or more sensor modules are described collectively as the one or more sensor modules 370, any one or more sensors or sensor modules within device 100 may operate independently of any one or more other sensors or sensor modules. Moreover, in addition to collecting, transmitting, and receiving signals or information to and from the one or more sensor modules 370 at the processor 305, any the one or more sensors of the one or more sensor module 370 may be configured to collect, transmit, or receive signals or information to and from other components or modules of the computing device 300, including but not limited to the database 340, the I/O module 350, or the interface 360.

As described above with respect to FIG. 1, the one or more accelerometers of the device 100 can be used to detect large-scale motions of a subject indicative of physical activity (e.g., steps, running, walking, swimming, etc.). The same accelerometers can be used to determine the onset of a sleep period based on the detection of a lack of motion. The one or more acoustical sensors can be used to detect and monitor heart rate. However, the sensitivity of the acoustical sensor (s) that detect heart rate aren't sensitive enough to detect relatively slow heart rate during sleeping. In one embodiment, upon determining that the subject is engaged in sleep, the sensitivity of the acoustical sensor(s) can be reconfigured to detect significantly low heart rate. Alternatively, the device 100 may comprise one or more acoustical sensors that are dedicated to, and configured for, detecting relatively slow heart rate during sleeping while one or more other acoustical sensors are used to detect regular heart rate during physical activity. To detect heart rate, an acoustical sensor can be configured to increase its sensitivity and sampling rate. Additionally, it may be advantageous to increase the sampling rate of an acoustical sensors for measuring relative slow heart rate during sleeping as compared to when measuring heart rate during physical activity. Again, regardless of the disparate sensitivity and/or sampling frequency between acoustical sensor settings for measuring regular and relative slow heart rate, the same acoustical sensor(s) in the device 100 of FIG. 1 can either be reconfigured upon detection of a sleep state, or alterative acoustical sensor(s) having a higher sensitivity can be activated during the sleep state. If an acoustical sensor that is calibrated for measuring regular heart rate during physical activity is used to measure relatively slow heart rate during sleeping, the amplitude of the output signal will not be great enough for accurate analysis. Conversely, if an acoustical sensor calibrated for measuring relatively slow heart rate during sleeping is used to measure regular heart rate during physical activity, the amplitude of the output signal will always be very large, resulting in a saturated signal that provides little useful information.

Figure 4:
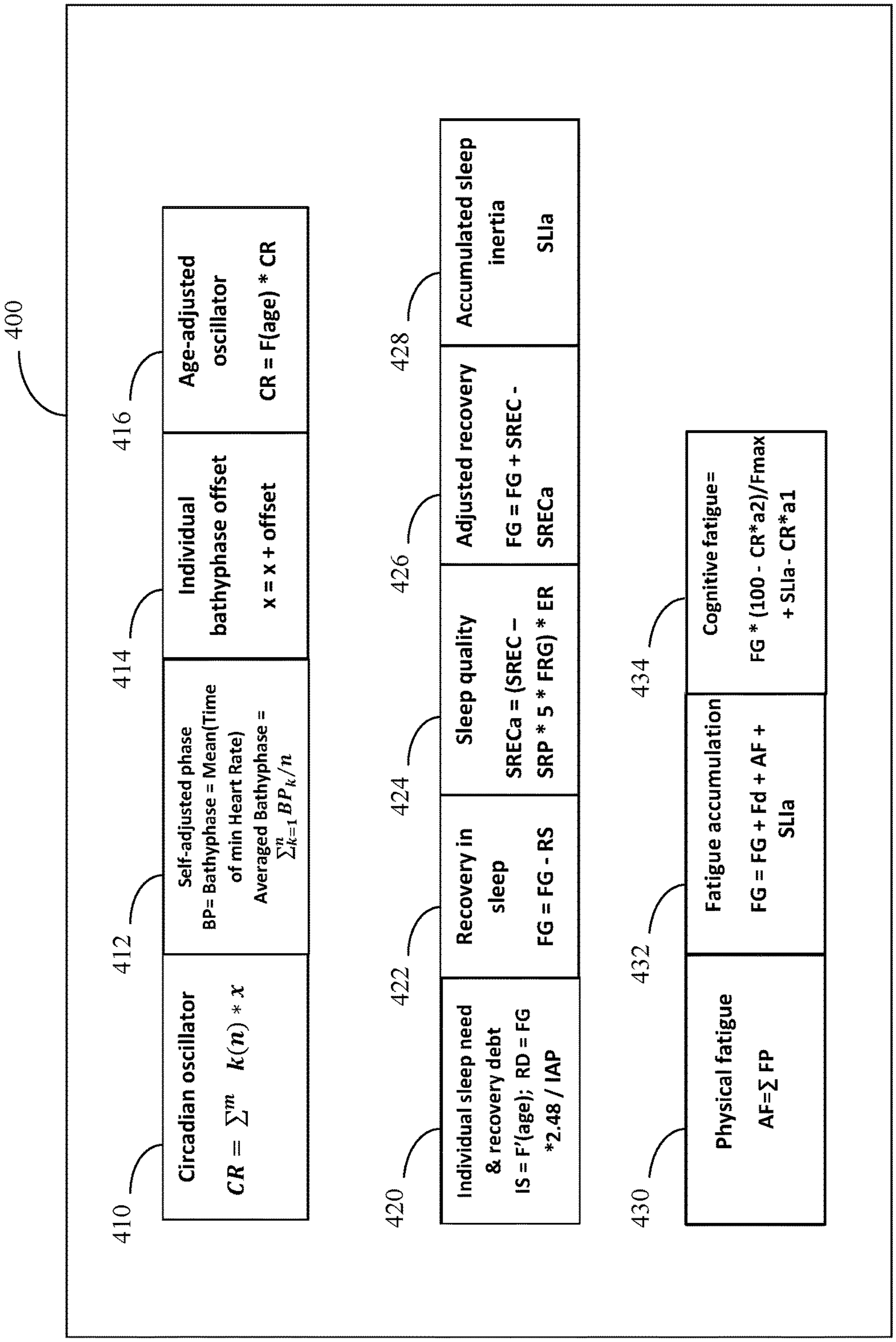
FIG. 4 depicts a series of steps of a technique for evaluating fatigue of a person.

FIG. 4 depicts a series of steps of a technique 400 for evaluating fatigue of a person. The technique 400 can be used to evaluate the level of physical and/or cognitive fatigue of a person. As shown, the technique 400 is depicted as a series of blocks 410-434. The technique 400 can be used to evaluate the fatigue level (FG) of a person (i.e., the person's physical fatigue). The technique 400 may be considered as including three components (or phases) including a circadian rhythm adjustment phase (i.e., blocks 410-416), a sleep recovery determination phase (i.e., blocks 420-428), and a fatigue evaluation phase (i.e., blocks 430-434).

The technique 400 can be executed using computing devices, such as the systems, hardware, and software described with respect to FIGS. 1-3. The technique 400 can be performed, for example, by executing a machine-readable program or other computer-executable instructions, such as routines, instructions, programs, or other code. The steps, or operations, of the technique 400 or another technique, method, process, or algorithm described in connection with the implementations disclosed herein can be implemented directly in hardware, firmware, software executed by hardware, circuitry, or a combination thereof. The technique 400 can be performed in whole or in part by the system 300 of FIG. 3.

Figure 5:
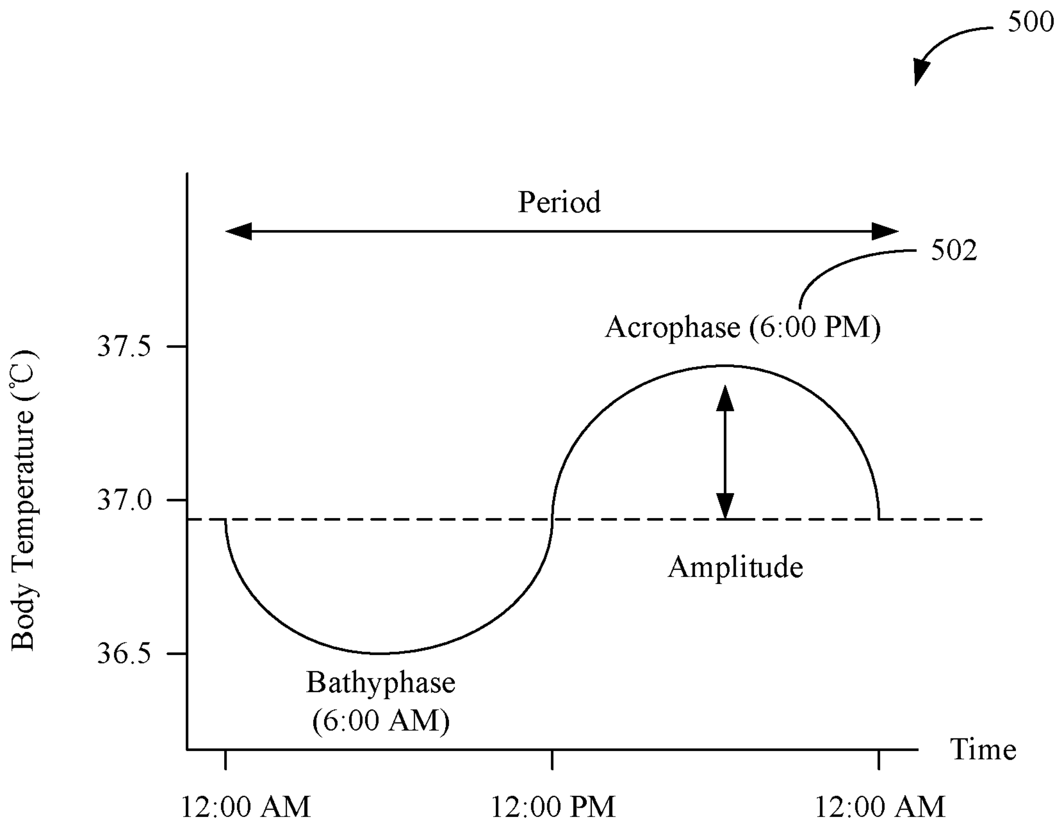
FIG. 5 illustrates a typical circadian rhythm oscillator.

At the block 410, the body temperature of a person throughout a day can be used to obtain a CR oscillator. The CR oscillator refers to a cyclic change of a human's body regulation during a day due to the intrinsic biological rhythm of the body. The CR oscillator may be obtained according to any known model for CR oscillators. FIG. 5 illustrates a typical CR oscillator 500. FIG. 5 illustrates that the body temperature of a human increases during the daytime and decreases during the nighttime. In general, a prominent peak 502 of the body temperature may be between 5:00 PM and 7:00 PM. Acrophase refers to the time-of-day of the maximum value of the body temperature. A position 504 indicates that acrophase may be around 6:00 PM. The lowest body temperature may be between 5:00 AM and 7:00 AM. Bathyphase refers to the time-of-day of the minimum value of the body temperature. The position of bathyphase may be around 6:00 AM.

At block 410 of FIG. 4, a rough smoothing approximation of the CR oscillator shown in FIG. 5 for the body temperature with extremums related to the acrophase and the bathyphase for a person can be obtained using equation (1):

$$CR = \sum_{n=0}^{m} k(n) * x^n \tag{1}$$

In equation (1), x designates a time of day in the form of: hour+min/60. For example, if the current time is 4:30 AM, then x can be 4.5 (i.e., 4+30/60=4.5). The CR oscillator indicates a relationship between the body temperature and time, n is an array of integers, m is related to a maximum number of the array of numbers (e.g., m=10 for the array of Table I), and k(n) is an approximating coefficient corresponding to n. The CR can be used to calculate the body temperature along the time. The CR can be a function, a model, or any type of mapping from time to body temperature that is indicative of circadian rhythm. At different times, the CR can be calculated as a value for further use by other metrics as further described herein. The CR is for a person individually. The shape of the circadian rhythm oscillator of equation (1) in the block 410 can be adjusted with the change of the k(n) coefficients. In some cases, k(n) and n can be generated based on an initial acrophase or bathyphase. The initial bathyphase and the acrophase are not calculated in equation (1). Based on different initial bathyphase and acrophase (which may be obtained from a model described with respect to FIG. 5), different CR functions can be generated with k(n) and n. The CR can be adjusted based on the changed bathyphase and acrophase. In another example, the approximation of the CR oscillator can be represented using any type of non-linear estimation.

Table I illustrates examples of n and k(n). Other values of n and corresponding k(n) can be also used to approximate the CR oscillator.

TABLE I

| n | k(n) |
|---|---|
| 0 | 0.50777144875419344 |
| 1 | 0.48301820592522526 |
| 2 | 0.03314458568798466 |
| 3 | 0.00631624822355558 |
| 4 | 0.00285117757082915 |

TABLE I-continued

| n | k(n) |
|---|---|
| 5 | 0.00041441708154086 |
| 6 | 0.00000292646100332 |
| 7 | 0.00000020255078533 |
| 8 | 0.00000000560510430 |
| 9 | 0.00000000005735723 |
| 10 | 0.50777144875419344 |

In the block 412, at least one of the acrophase or the bathyphase of the CR oscillator obtained by equation (1) can be adjusted based on individual characteristics of the person. As such, the block 412 may be referred to as a self-adjusted phase.

As is known, the acrophase and the bathyphase for body temperature are not the same for all persons. The acrophase and the bathyphase may depend on the lifestyle of the person. For example, the acrophase and the bathyphase may depend on the time that the person goes to bed or falls asleep. For example, the acrophase and the bathyphase may frequently change for shift-workers or humans traveling between different time zones. Thus, adjusting the CR oscillator can mean or include adjusting at least one of the acrophase or the bathyphase of a reference CR oscillator.

The bathyphase can be adjusted using equation (2) and equation (3) in the block 412, which uses an averaged bathyphase (AB) to improve the estimation accuracy of the bathyphase. The averaged bathyphase obtained using equation (3) may also be referred to as a corrected (or adjusted) bathyphase.

$$BP = Bathyphase = \text{Mean(Time of heart Rate)} \quad (2)$$

$$AB = \text{Averaged } Bathyphase = \sum_{k=1}^{n} BP_k/n \quad (3)$$

The regulation of heart rate correlates with body temperature. For example, a minimum heart rate in sleep may correspond to a minimum body temperature. Equation (2) can be used to calculate the time of the bathyphase, which is computed as the mean time of a set of heart rates. As can be appreciated, the heart rate can fluctuate. That is, a person may have different heart rates at different times. Thus, given the set of heart rates, the mean time can be used to be the bathyphase. In an example, a set of time slots (e.g., 1 minute per time slot) can be used to calculate the bathyphase in equation (2), in which the set includes several time slots and one time slot includes a minimum heart rate, in which the difference between heart rate from other time slot and minimum heart rate is less than a threshold number of heart beats (e.g., 1 or 2 beats). To illustrate, during sleep, the heart rate of a person is obtained per time slot (e.g., 1 minute, 5 minutes, or some other time slot) resulting in sleep-session heart rates. The minimum values (sleep-session minima) in the sleep-session heart rates are identified. Any heart rate in the sleep-session heart rates (including the sleep-session minima) that is within threshold number of heart beats is added to the set of heart rates. BP is then calculated as the mean value of the sleep-session heart rates that are in the set of heart rates. In an example, the time slots can be consecutive time slots, can be random time slots, or selected in any number of ways.

A wearable device, such as the wearable device 100 of FIG. 1, can be used to measure heart rate properties in sleep over a period of time (e.g., 3 nights, 5 nights, a rolling window of a predefined number of days, etc.). In an example, the heart rate properties may be measured using an acoustical sensor, which may be included in the sensor modules 370 of FIG. 3. In equation (3), the AB can be calculated by averaging the bathyphase (BP) calculated (using equation (2)) over n nights. For example, the AB for the last three nights (i.e., n=3) can be used as a corrected bathyphase to reduce the estimation inaccuracy of the bathyphase. Based on the corrected bathyphase, the acrophase can be corrected based on equation (4), in which T designates a fixed time difference between the bathyphase and acrophase in a day. (e.g., T=12 hours). An initial (e.g., default or preset) bathyphase value can be used until sufficient heart rate data is available to calculate the bathyphase using equation (2). The initial bathyphase value can be 5. That is, the mean time of the bathyphase can be assumed to be 5 AM.

$$acrophase = T + bathyphase \quad (4)$$

In the block 414, an individual bathyphase onset latency can be used to further adjust the CR oscillator.

As described above with respect to equation (3), the averaged bathyphase (AB) is used as the corrected bathyphase. When the bathyphase is corrected (to ensure the accuracy of the CR oscillator), the corrected time offset, which is the time difference between the AB and the initial bathyphase, can be added to the time variable x in equation (1) in the block 410 to adjust the CR oscillator. As such, the function of CR can be thought as being horizontally moved left or right by offset units. The corrected time offset refers to the individual bathyphase onset latency. To illustrate, the previous bathyphase may be 5:00 AM and the corrected AB for the last three night may be 6:00 AM. In that case, the offset (time difference) in equation (5) in the block 414 between the AB and the previous bathyphase is 1 hour that can be added to time variable x in equation (1) in the block 410 to adjust the CR oscillator.

$$x = x + \text{offset} \quad (5)$$

Figure 8A:
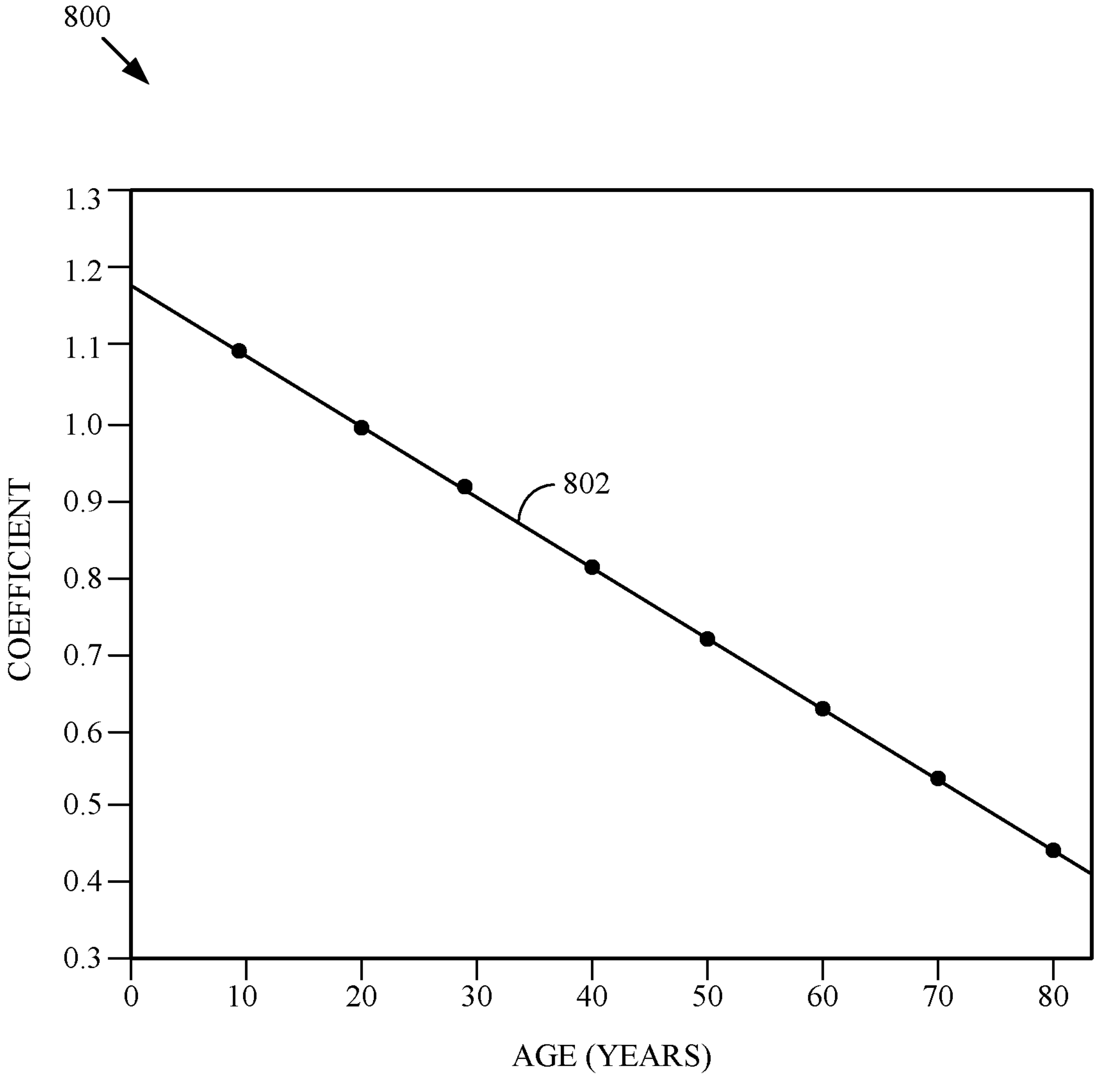
FIG. 8A illustrates a plot of a function that can be used to obtain an age-adjusted oscillator according to a first example.
Figure 8B:
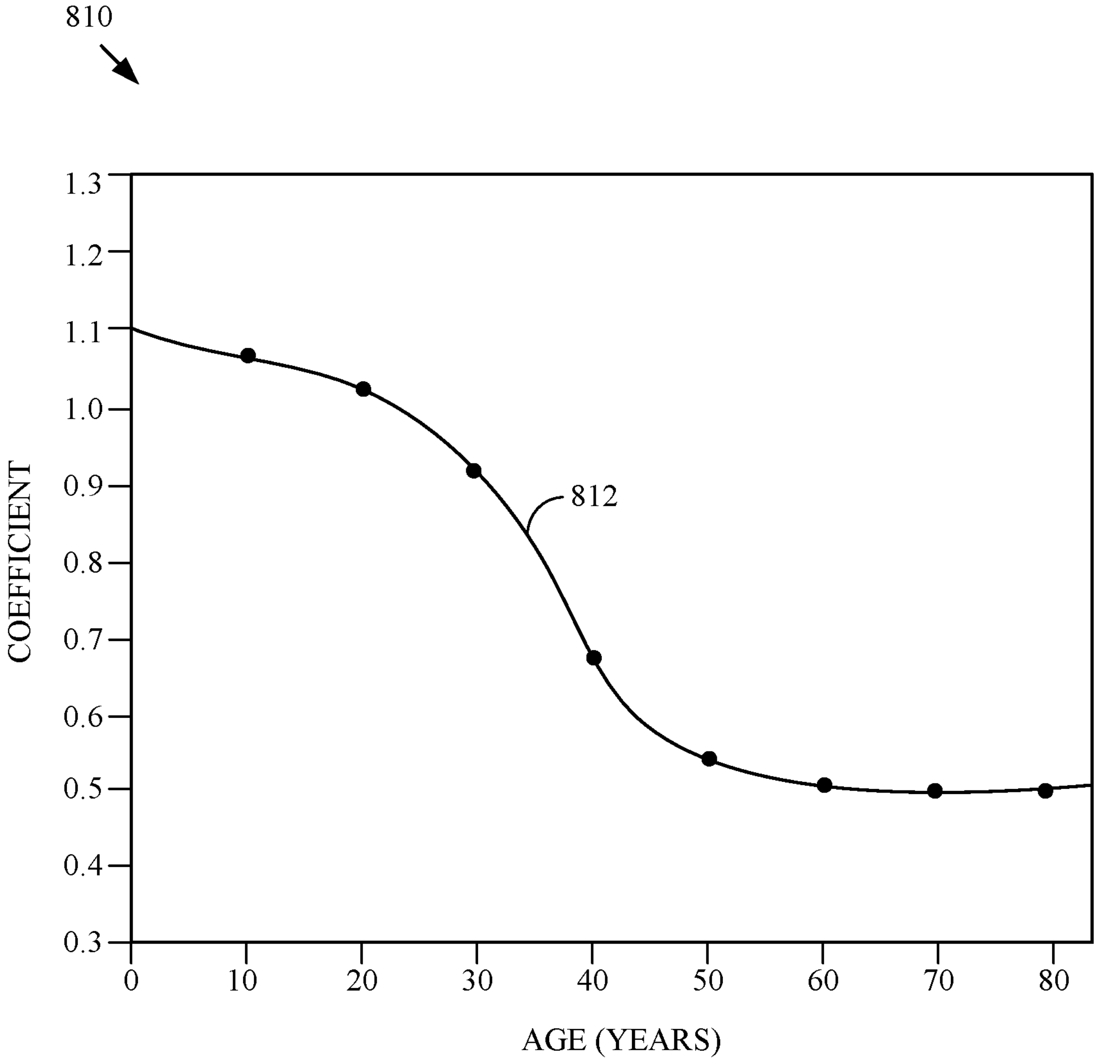
FIG. 8B illustrates a plot of a function that can be used to obtain an age-adjusted oscillator according to a second example.

In the block 416, an age-adjusted oscillator F (age) can be further used to adjust the CR oscillator. The amplitude of the acrophase and the bathyphase can change with aging. For example, the peak of the acrophase and the bathyphase may be more prominent in younger people. To illustrate, the amplitude for 8 to 12 years old children is typically 10% larger than the amplitude for adults. Statistical data of amplitudes by ages can be used to obtain the age-adjusted oscillator F(age) to approximate an estimation of the dependency between the amplitude and the different ages. In a first example, F(age)=(−0.00975869)*age+1.18496, in which the variable 'age' designates the age of a person, in years. To illustrate, if a person is 15 years old, 'age' is equal to 15. This function is illustrated in FIG. 8A. FIG. 8A illustrates a plot 800 of a function (a line 802) that can be used to obtain F(age) according to the first example. In a second example, F(age)=0.566088−42.4118/(−77.3604−0.44013*$e^{0.153825*age}$. This function is illustrated in FIG. 8B. FIG. 8B illustrates a plot 810 of a function (a line 812) that can be used to obtain F(age) according to the second example. F(age) can be used for additional individual adjustment. In another example, the biological age (i.e., the age rounded to the closest whole number of years) can be used. The CR oscillator can be adjusted by multiplying the age-adjusted oscillator F(age) to adjust the amplitude for different age groups, which is depicted in equation (6) in the block 416.

$$CR = F(\text{age}) * CR \tag{6}$$

To restate, the body temperature of a person in a day can be used to obtain the reference CR oscillator, and the reference CR oscillator can then be adjusted using equations (2)-(6) through self-adjusting the acrophase and the bathyphase, the individual bathyphase onset latency adjustment, and the age-adjusted oscillator. The reference CR oscillator is specific to the person him/herself. In some implementations, referring back to FIG. 2, the circadian rhythm oscillator can be obtained by the fatigue evaluation tool 204.

In the block 420, equations (7) and (8) can be used to calculate an individual sleep need (IS) and a recovery debt (RD), respectively.

$$IS = F'(\text{age}), \tag{7}$$

$$RD = FG * 2.48 / IAP, \tag{8}$$

$$\text{Individual awakening period } (IAP) = 24 * 60 - IS \text{ (in minutes)}, \tag{9}$$

Figure 9:
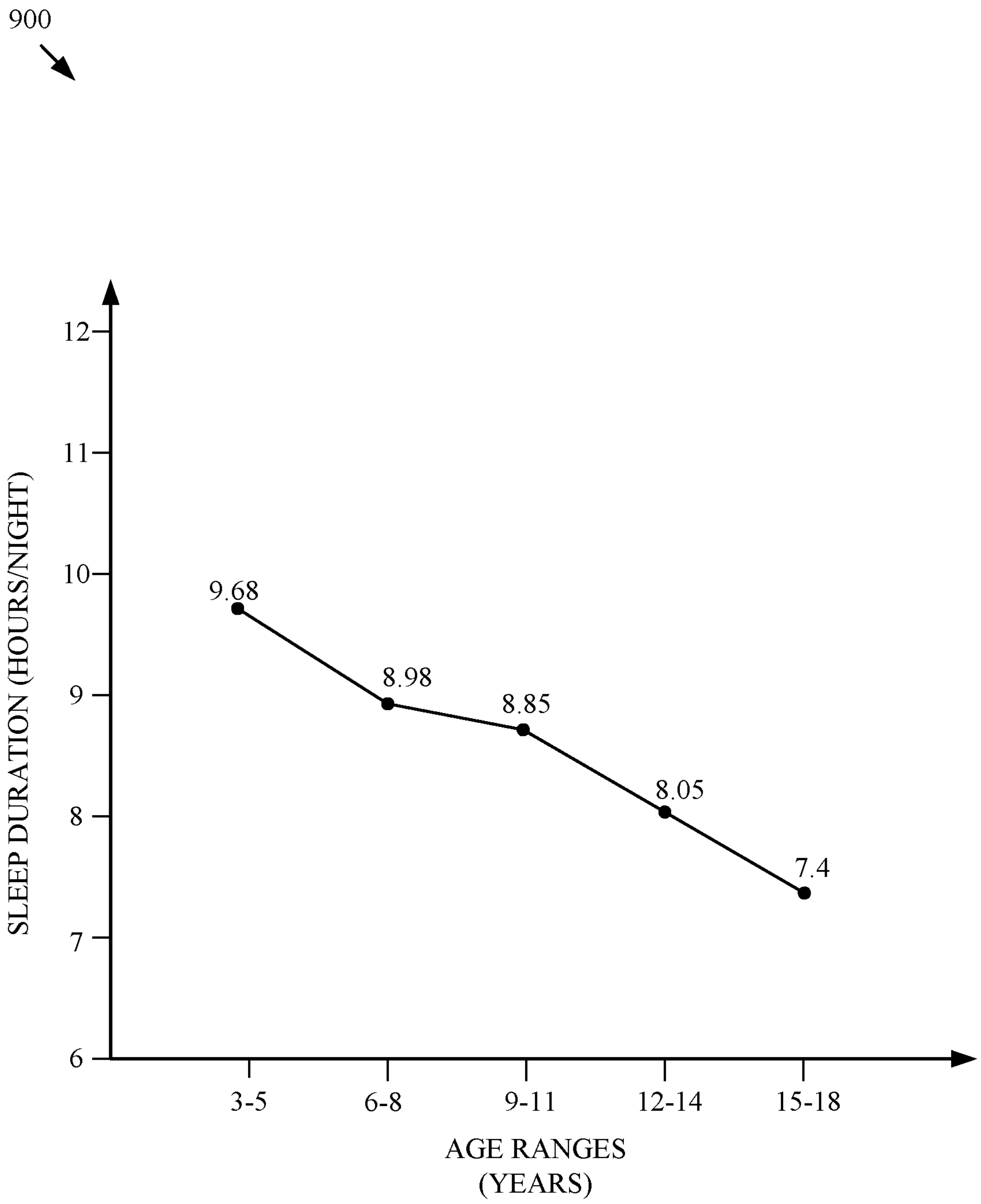
FIG. 9 illustrates a relationship between age and individual sleep need.

Note that an age-related function F'(age) herein in equation (7) is different from the age-adjusted oscillator F(age) in equation (6) in the block 416. In equation (7), the IS can be initially estimated by the age-related function F'(age). Different age groups have different individual sleep needs. Table II illustrates examples of age and individual sleep need. Until sufficient data on the person's sleep are accumulated, the age of the person can be used to assess the sleep needs of the person according to Table II. For example, for children below 5 years old, an individual sleep need of 9.68 hours can be used; and for persons above 60 years old, an individual sleep need of 7.24 hours can be used. Through the age-related function F'(age) in equation (7), the IS can be estimated for different age groups. F'(age) can be as illustrated in FIG. 9. FIG. 9 illustrates a relationship between age and individual sleep need. When sufficient sleep data on the individual are accumulated, it may no longer be necessary to use the age to assess the individual sleep needs. In an example, sufficient sleep data can mean sleep data accumulated for at least the last 30 nights. A median of the sleep onset latency (SOL) can be calculated for the last, e.g., 30 sessions. A sleep session can refer to, for example, a night of sleep. A period of sleep may be determined to be a sleep session if it is longer than a threshold time (e.g., 4 hours). This is to distinguish a sleep session from a simple nap. A subset of the sleep sessions can be selected, e.g., 15 sleep sessions. A median (or some other statistic, such as the average) of the total sleep time of the selected sessions is calculated. The median (referred to as the duration of an individual sleep) indicates and can be used as the individual sleep need (IS).

Based on the IS, an individual awakening period (IAP) can be calculated using equation (9), in which the IS is expressed in minutes, 24*60 indicates 24 hours in minutes. IAP is a duration of wakefulness for an individual in a day. Based on the IAP, the RD (i.e., the amount of needed recovery time for the current amount of fatigue before sleep) can be calculated using equation (8), in which 2.48 is an empirically derived coefficient, and FG indicates the obtained amount of fatigue before sleep.

TABLE II

| age | Normal sleep duration, h + min/60 |
|---|---|
| <5 | 9.68 |
| 6-8 | 8.98 |
| 9-11 | 8.85 |
| 12-14 | 8.05 |
| 15-18 | 7.4 |
| 19-60 | 7.12 |
| >60 | 7.24 |

In some implementations, during wakefulness, the amount of the RD is regularly computed (such as every minute and using equation (8)) to dynamically indicate the needed recovery time. In an example, the amount of the RD may be computed on a regular basis (e.g., every minute) because the person may be about to undertake an activity but is expected to be fatigued by then. As such, the person may take a nap to recover. The person may set an alarm that goes off when the recovery level or the fatigue level are such that the person has sufficiently recovered so as to be able to undertake the activity.

In the block 422, equation (10) can be used to update fatigue level (FG) by decreasing recovery in sleep (RS) at regular intervals (e.g., every minute). The recovery in sleep (RS) can be calculated through the recovery debt (RD) in the block 420 and the CR oscillator (CR) in the block 416 in equation (11).

$$FG = FG - RS \tag{10}$$

$$RS = \max((RD - 0.5 * CR), 5) \tag{11}$$

The recovery in sleep (RS) can be calculated at regular intervals (e.g., every minute). In some implementations, 5 is maximum decrease in fatigue per time unit (e.g., one minute). When the RS is above 5, the RS is set to 5. In equation (11), a first coefficient (i.e., 0.5) can also be set to a first value within a first range [0, 10]. A second coefficient (i.e., 5) can also be set to a second value within a second range [4, 10]. During sleep, the FG is being decreased by the RS every minute. The maximum decrease in fatigue per time unit and the first coefficient were empirically derived and other values are possible, depending on the implementation.

In the block 424, equation (12) can be used to calculate adjusted sleep recovery ($SREC_a$) using sleep recovery (SREC), sleep recovery point (SRP), fragmentation (FRG), and excess heart rate (ER).

$$SREC_a = (SREC - SRP * 5 * FRG) * ER \tag{12}$$

In equation (12), the SREC is an amount of recovery from fatigue during sleep, SRECa is an adjusted SREC based on sleep quality. That is, the SREC can be adjusted based on a determined sleep quality. SREC can be calculated as the difference between RTBS and RTIS (i.e., SREC=RTBS−RTIS), in which the RTBS indicates the last fatigue value before sleep, and the RTIS indicates the last fatigue value before waking. The SREC indicates the total energy recovered during sleep. On the other hand, the recovery in sleep (RS) calculated in equation (11) indicates a recovery value for fatigue per time unit (e.g., per minute) during sleep. In equation (12), the SRP is equal to the SREC divided by sleep duration in the current day (i.e., SREC/(sleep duration)). Sleep duration refers to the length of time of a sleep sessions within a day. In general, sleep quality can be influenced by two main factors that include the FRG and the ER, in which the ER is an excess of the previous night's sleep heart rate over a median sleep heart rate during consecutive nights and the FRG is the number of uninterrupted sleep segments during a night. To illustrate, if a person is determined (using sleep data) to have woken up two times during the night, then the number of uninterrupted sleep segments is 3. The larger the FRG, the poorer the sleep quality. In equation (13), the ER can be calculated by sleep heart rate (SHR) and median sleep heart rate level (MSL).

$$ER = 1 - 0.5 * (SHR - MSL)/MSL \tag{13}$$

In equation (13), the SHR can be a median heart rate during sleep, and the MSL can be a median of sleep heart rate during last several nights. In some implementations, the MSL can be a median of sleep heart rate during last 30 nights. MSL can be considered to be an optimal heart rate in sleep for the individual. A current sleep heart rate (SHR) that is higher than MSL may be said to hurt the sleep quality. On the other hand, a sleep heart rate that is lower than MSL (and correspondently ER<1) can be ignored. As such, in an example, if the ER is less than 1, then the ER is set to 1. In an example, if the SHR is less than the MSL, then the ER is set to 1. In some implementations, if the sleep duration is greater than the individual sleep need in the block 420, the $SREC_a$ can be adjusted by adding 15×SRP as shown in equation (13'). The adjustment reflects that prolonged sleep can provide recovery but only to a certain maximum extent. A coefficient (i.e., 15) in equation (13') can also be set to a value within a range [0, 100].

$$SREC_a = SREC_a + 15 \times SRP \tag{13'}$$

Based on the SREC, SRP, FRG, and ER, the $SREC_a$ can be calculated as the adjusted sleep recovery to further adjust the FG in the block 426 when sleep is done (e.g., completed, when the person awakes). As such, the FG is updated based on the recovery debt (RD) during sleep and then further updated based on the adjusted sleep recovery $SREC_a$. In an example, sleep may be determined to be done when the person is no longer in a prone position after being determined to have been sleeping. In the block 426, equation (14) can be used to adjust the FG obtained as described with respect to the block 422. When sleep is done, the fatigue is further adjusted to add the difference between the SREC and the $SREC_a$.

$$FG = FG + SREC - SREC_a \tag{14}$$

The effect of equation (14) can be described as follows. If a person has a relatively good sleep quality night (e.g., a large $SREC_a$), the FG can be further reduced after sleep based on equation (14). For example, if the sleep quality is good with a smaller fragmentation (FRG), the $SREC_a$ becomes bigger so that the FG is further reduced. With a relatively poor sleep quality night (a smaller $SREC_a$), the FG can be further increased after sleep. For example, if the sleep quality is bad with a greater fragmentation (FRG), the $SREC_a$ becomes smaller so that the FG is further increased.

In the block 428, an accumulated sleep inertia (SLIa) can be used to adjust the FG. Sleep inertia occurs at two transition states: from sleep to wakefulness (a first stage), and from wakefulness to sleep (a second stage). That is, the SLIa can be calculated at two stages. In the first stage, the SLIa can be accumulated by sleep inertia in sleep (SLIs) at regular intervals (e.g., every minute) during a time range in sleep shown in equation (15)

$$SLIa = SLIa + SLIs \tag{15}$$

$$SLIs = k \times L \times \frac{e^{k*(xo-Ts)}}{\left(e^{(k*(xo-Ts)+1)}\right)^2} \tag{16}$$

The SLIs can be calculated using equation (16) in which L is a constant that is indicative of a maximum performance units, k is the steepness of the SLIa, x0 can the midpoint of time domain for calculating sleep inertia, and Ts is the time from sleep onset. Equation (16) reflects the logistic nature of the sleep inertia and gives an instantaneous score of inertia. The SLIs is calculated every minute during the time range in sleep. In some implementations, L is equal to 144, k is equal to 0.1, and the time range in sleep can be the first 120 minutes in sleep. The constant x0 is empirically derived and can be 40, 60, or 120. The constant x0 reflects the fact (or point in time within sleep) where the contribution of sleep inertia becomes negligible. Out of the time range in sleep, the SLIs is not calculated.

In the second stage, the SLIa can be reduced by sleep inertia compensation in wakefulness (SLIc) at regular intervals (e.g., every minute) during a time range in wakefulness shown in equation (17).

$$SLIa = SLIa - SLIc \tag{17}$$

$$SLIc = 144 \times sk1 \times 120 \times e^{\left(\frac{(120}{sk2} - \frac{sk1*120}{Ta+1}\right)/(Ta+1)^2} \tag{18}$$

The SLIc can be calculated using equation (18), in which sk1 and sk2 can be two constant values, Ta can be the time in wakefulness (e.g., the time since waking). The SLIc can be calculated at regular intervals (e.g., every minute) during the time range in wakefulness. In some implementations, if the last stage in sleep is deep sleep, sk1 can be equal to 0.32 and sk2 can be equal to 375. If the last stage in sleep is not deep sleep, sk1 can be equal to 0.16 and sk2 is equal to 750. In some implementations, when the individual is not in deep sleep, sk1 can be set to a first value within a first range [0, 0.5]. When the individual is in deep sleep, sk1 can be set to a second value within a second range [0, 1]. In some implementations, regardless of sleep state, sk2 can be a value within a range [1, 1000]. The values of sk1 and sk2 are empirically derived and other values are possible. The time range in wakefulness can be the first 120 minutes in wakefulness. Out of the time range in wakefulness, the SLIa is not calculated. In some implementations, if the SLIa is less than or equal to zero, the SLIa is set to zero and the calculation of SLIc is stopped. After the two stages, if the SLIa is greater than zero, the SLIa is added to the FG.

Referring back to FIG. 2, the block 420 of individual sleep need and recovery debt, the block 422 of recovery in sleep, the block 424 of adjusted sleep recovery, the block 426 of adjusting the FG, and the block 428 of the calculation of an accumulated sleep inertia (SLIa) can be performed by the sleep recovery tool 204.

In the block 430, equation (19) can be used to calculate the total of physical fatigue (AF) during wakefulness. The total of physical fatigue (AF) is the sum of the fatigue (such as due to physical activities) during wakefulness.

$$AF = \sum FP \text{ (Heart rate)} \tag{19}$$

The AF is accumulated at regular intervals (e.g., each minute) during wakefulness by a fatigue point (FP). That is, for example, at the end of each interval, an FP value is added to the AF. The value of the FP correlates with heart rate. The value of the FP can be calculated at regular intervals (e.g., every minute) based on heart rate. In some implementations, if the heart rate is less than 30% of maximal oxygen consumption (VO2max), the FP=0 and the AF doesn't change. If the heart rate is greater than 30% and less than 50% of VO2max, the FP=0.288. If the heart rate is greater than 50% of VO2max, the FP=0.6552. During sleep, the FP is equal to 0.

In the block 432, equation (20) can be used to calculate the accumulated FG during wakefulness. During wakefulness, the FG can be accumulated at regular intervals (e.g., every minute) by a Fd, in which the Fd is a constant value that indicates a continuous increase of the fatigue at regular intervals (e.g., every minute). After completing the calculation of the total of physical fatigue (AF), the AF and the accumulated sleep inertia (SLIa) can be also added to the FG.

$$FG = FG + Fd + AF + SLIa \tag{20}$$

In the block 434, equation (21) can be used to calculate cognitive fatigue. In equation (21), al is a coefficient, Fmax indicates maximum fatigue after several days of full wakefulness, CR is the CR oscillator, and SLIa is the accumulated sleep inertia. In some implementations, Fmax is the maximum fatigue after full 4 days' wakefulness.

$$\text{Cognitive fatigue} = FG \times \frac{100 - CR * a2}{F\max} + SLIa - CR \times a1, \tag{21}$$

Referring back to FIG. 2, the block 430 of the total of physical fatigue (AF) during wakefulness, the block 432 of the accumulated fatigue (FG) during wakefulness, and the block 434 of cognitive fatigue can be performed by the fatigue evaluation tool 204.

Figure 6:
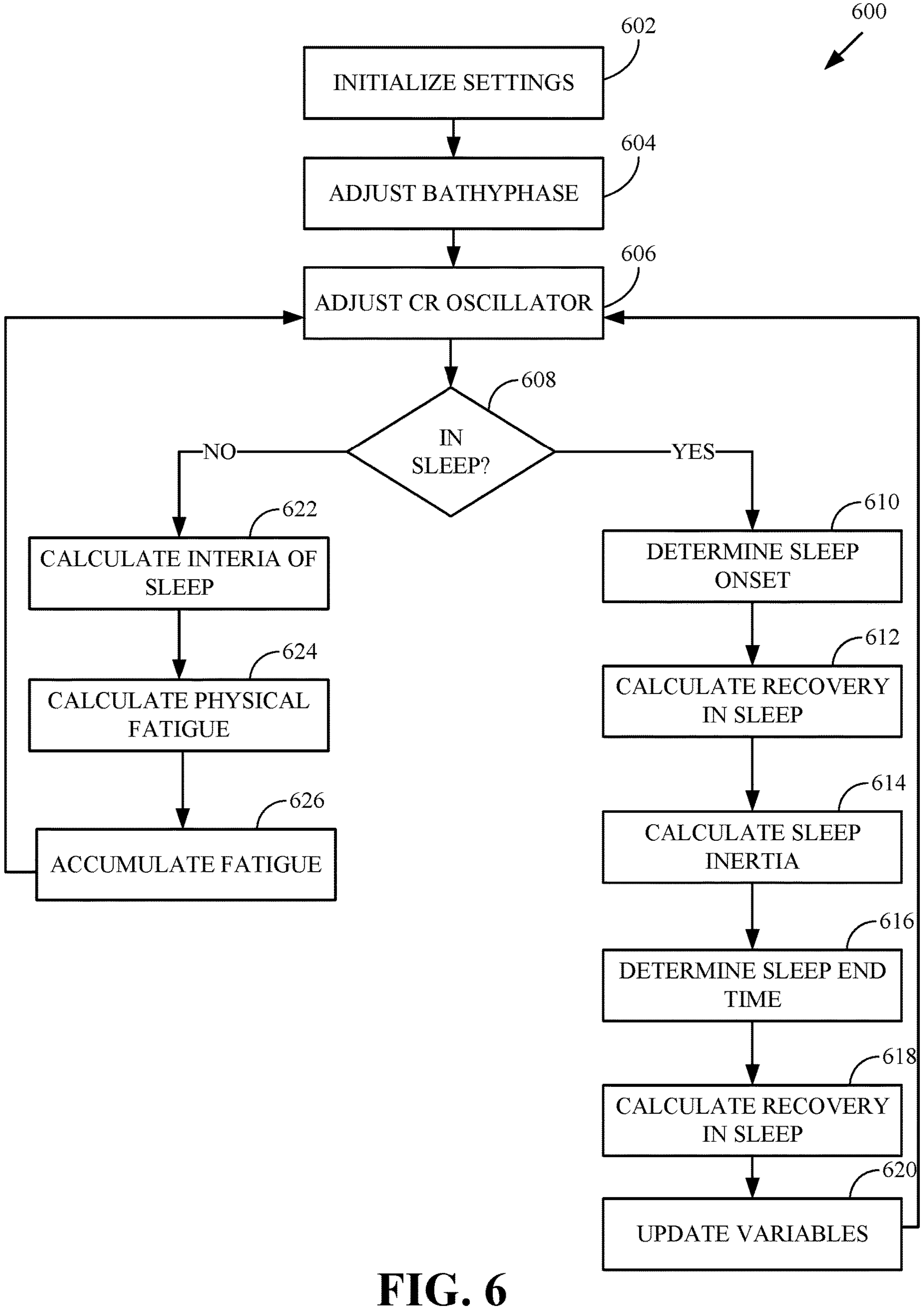
FIG. 6 illustrates an example of a technique for evaluating fatigue of a person.

FIG. 6 is a flowchart of an example of a technique 600 for evaluating fatigue of a person. The technique 600 can be implemented at least in part by a device, such as the device 100 of FIG. 1. In an example, different aspects of the technique 600 can be implemented in part by respective tools of the system 200 of FIG. 2. The technique 600 can be implemented, for example, as a software program that may be executed by computing devices such as a device that may be in communication with a wearable device or receive acoustical sensor signals obtained using an acoustical sensor of the wearable device. The software program can include machine-readable instructions that may be stored in a memory such as the RAM 310, the ROM 320, or the storage 330 of FIG. 3, and that, when executed by a processor, such as the processor 305 of FIG. 3, may cause the computing device to perform the technique 600. The technique 600 can be implemented using specialized hardware or firmware.

At 602, an individual sleep need (IS), a recovery debt (RD), a bathyphase, and an age-adjusted oscillator can be initially set up. The IS can be initially set up by age-related function F'(age) in equation (7). Depending on the age of the person, the IS can be set up to be a corresponding value (e.g., 8.85 hours for age 9 to 11) according to Table II. The RD can be set up based on equation (8) using fatigue level (FG) and individual awakening period (IAP) of the person. An initial bathyphase value can be used. For example, the initial bathyphase value can be 5. That is, the mean time of the bathyphase can be assumed to be 5 AM. Correcting offset (COF) for the bathyphase can be initially set up to 0. The age-adjusted oscillator can be set up by a circadian rhythm (CR) oscillator and an age-adjusted oscillator F (age) in equation (6).

At 604, the bathyphase can be adjusted to be equal to a corrected bathyphase time (CBT). The CBT is equal to an averaged bathyphase in equation (3). In an example, the bathyphase can be further adjusted by the COF based on equation (5). At 606, the CR oscillator can be further adjusted based on the adjusted bathyphase to correctly indicate the person's temperature with extremums related to the adjusted bathyphase. At operation 508, is it checked whether the person is in sleep. If the person is in sleep, the technique 600 proceeds to update the FG using steps 610-620. If the person is not in sleep, the technique 600 proceeds to update the FG using steps 622-628.

At 610, a sleep onset time is determined for the person. The sleep onset time can be used to adjust the bathyphase. At 612, a recovery in sleep (RS) can be calculated at regular intervals (e.g., every minute) based on equation (11). During sleep, the FG can be decreased by the RS at regular intervals (e.g., every minute). At 614, sleep inertia can be calculated. The sleep inertia can be accumulated from sleep to wakefulness based on equation (15), and can be reduced from wakefulness to sleep based on equation (17). At 616, a sleep end time can be determined stored. A sleep duration can then be calculated at a difference between the sleep onset and the sleep end time.

At 618, sleep recovery (SREC) can be calculated. SREC can be calculated as the difference between last fatigue value calculated before sleep and last fatigue value measured during sleep. The SREC indicates the total of energy recovered during sleep. In an example, the SREC can be adjusted based on sleep quality. The adjusted sleep quality can calculated using equations (12) and (13'). In an example, the FG can be further adjusted to add the difference between the SREC and the $SREC_a$, shown in equation (14). At 620, the technique 600 updates certain variables based on additional collected data. For example, based on the stored sleep onset, an average sleep onset (ASO) can be calculated based on all stored sleep onset for several days. The ASO can be fed back to the operation 606 to further adjust the bathyphase. Additionally, the mean time of minimum heart can also be updated.

At 622, during a time range in wakefulness, an accumulated sleep inertia (SLIa) can be reduced by sleep inertia compensation (SLIc) at regular intervals (e.g., every minute). The SLIc can be calculated using equation (18). The SLIa can be updated using equation (17). At 624, during wakefulness, the total of physical fatigue (AF) can be calculated based on equation (19). The AF can be calculated as the sum of the fatigue due to physical activities during wakefulness. The AF can be accumulated at regular intervals (e.g., each minute) during wakefulness by a fatigue point (FP). The value of the FP correlates with heart rate.

At 626, based on equation (20), during wakefulness, the FG can be accumulated at regular intervals (e.g., every minute) by a Fd, which is a constant value that indicates a continuous increase of the fatigue at regular intervals (e.g., every minute). After completing the calculation of the total of physical fatigue (AF), the AF and the accumulated sleep inertia (SLIa) can be also added to the FG. Equation (21) can be used to calculate cognitive fatigue. In equation (21), al is a coefficient, Fmax indicates maximum fatigue after several days' full wakefulness, CR is the CR oscillator, and the SLIa is the accumulated sleep inertia. The FG can be fed back to the operation 606 to calculate the RD, and the FG as a basis can be updated in a new day.

Figure 7:
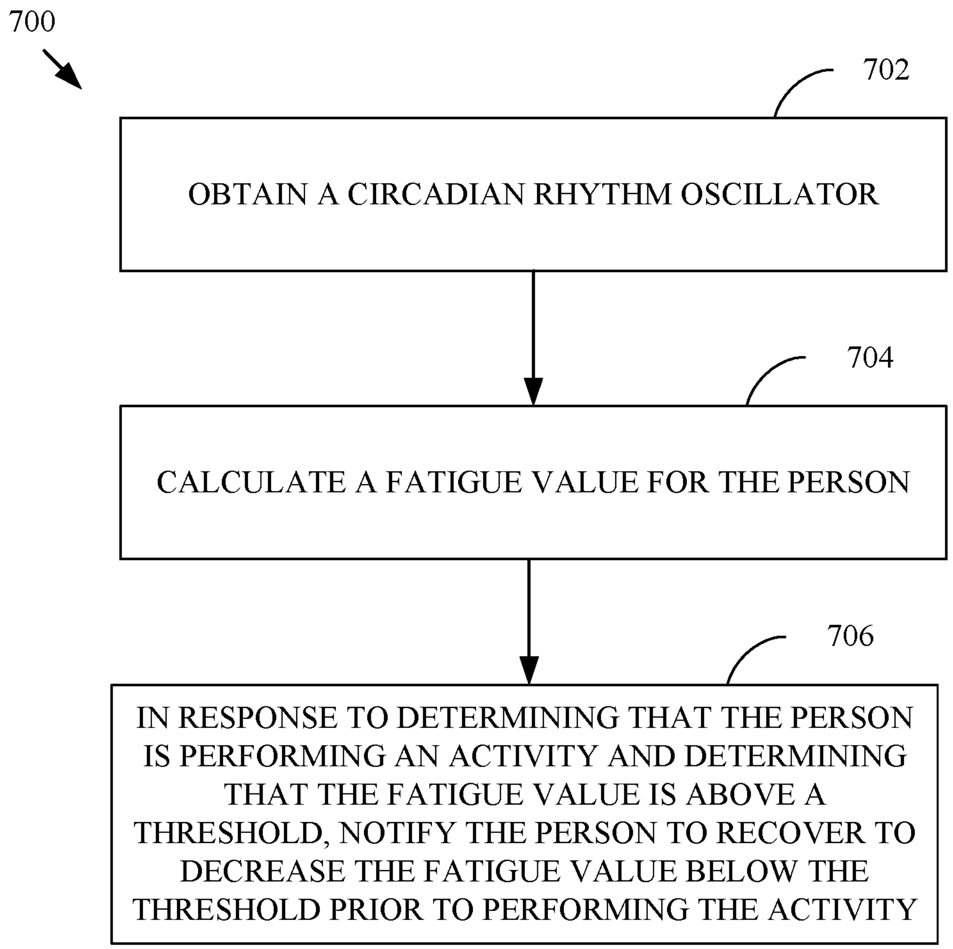
FIG. 7 illustrates an example flowchart for assessing the fatigue level of a person.

FIG. 7 is an example of a flowchart of a technique 700 for assessing the fatigue level of a person. The technique 700 can be implemented at least in part by a device, such as the device 100 of FIG. 1. In an example, different aspects of the technique 700 can be implemented in part by respective tools of the system 200 of FIG. 2. The technique 700 can be implemented, for example, as a software program that may be executed by computing devices such as a device that may be in communication with a wearable device or receive acoustical sensor signals obtained using an acoustical sensor of the wearable device. The software program can include machine-readable instructions that may be stored in a memory such as the RAM 310, the ROM 320, or the storage 330 of FIG. 3, and that, when executed by a processor, such as the processor 305 of FIG. 3, may cause the computing device to perform the technique 700. The technique 700 can be implemented using specialized hardware or firmware.

At 702, a circadian rhythm (CR) oscillator can be obtained for the person based at least in part on a bathyphase time. Using FIG. 4 as an example, at a block 410, a CR oscillator can be obtained that illustrates that the body temperature of the person increases during the daytime and decreases during the nighttime. In some implementations, a bathyphase time, which refers to the time-of-day of the minimum value of the body temperature, can be around 6:00 AM. The CR oscillator can be obtained using equation (1) at the block 410.

At 704, a fatigue value can be calculated for the person. The fatigue value may be separately calculated during two phases. In response to determining that the person is in sleep, subtracting a sleep recovery unit from the fatigue value in a time unit wherein the sleep recovery unit is calculated based on the CR oscillator and a recovery debt. In some implementations, using FIG. 4 as an example, at a block 422, the sleep recovery unit (e.g., recovery in sleep) can be calculated in equation (11) based on the recovery debt in a block 420 and the CR oscillator in a block 416. The recovery debt can be calculated based on equations (7), (8), and (9) in the block 420. The fatigue value can be updated based on equation (10) at regular intervals (e.g., every minute).

In some implementations, an individual sleep need for the person can be set up based on an age of the person. The recovery debt can be calculated for the person based on a previous fatigue value and a previous individual awakening period from a previous day. Using FIG. 4 as an example, in the block 416. an individual sleep need can be calculated based on equation (7). The previous individual awakening period (IAP) can be calculated based on equation (9). Based on the previous IAP from a previous day and a previous fatigue value, the recovery debt can be calculated based on equation (8).

In some implementations, when the person is in sleep in a first time range, a total sleep inertia can be accumulated by an inertia in sleep in the time unit. Using FIG. 4 as an example, in a block 428, an accumulated sleep inertia (e.g., SLIa) can be accumulated by sleep inertia in sleep (e.g., SLIs) based on equations (15) and (16) during a time range from sleep to wakefulness.

In some implementations, on a condition that the person is not asleep within a second time range, the total sleep inertia can be subtracted by an inertia out of sleep. Using FIG. 4 as an example, in the block 428, the SLIa can be subtracted by sleep inertia compensation in wakefulness (SLIc) based on equations (17) and (18) during a second time range.

In some implementations, in response to determining that the person is not asleep, the fatigue value can be accumulated by a base fatigue factor and a base physical fatigue factor, wherein the base physical fatigue factor is based on a heart rate of the person. Using FIG. 4 as an example, during wakefulness, the fatigue value can be accumulated at regular intervals (e.g., every minute) by a Fd in a block 432. The Fd refers to the base fatigue factor. The total of physical fatigue (AF) is accumulated during wakefulness by a fatigue point (FP). The FP refers to the base physical fatigue factor that correlates with heart rate of the person. The fatigue value can be accumulated based on equation (20) in the block 432.

In some implementations, the fatigue value can be adjusted using the total sleep inertia. Using FIG. 4 as an example, the SLIa can be added to the fatigue value based on equation (20).

At 706, in response to determining that the person is performing an activity and determining that the fatigue value is above a threshold, the person can be notified to recover to decrease the fatigue value below the threshold prior to performing the activity. For example, the person cannot perform a hard workout unless the fatigue value of the person is below the threshold. In some cases, the person can have a rest to recover from fatigue to decrease the fatigue value below the threshold. The notification (e.g., alert) may be displayed on a wearable device, such as the device 100 of FIG. 1. The notification may be displayed on a personal device, such as mobile device. The notification may be displayed or transmitted to some other device and using different modalities.

In an example, the person may indicate that they are expecting to be performing a particular activity at a particular time. In an example, the user may provide such input using via an application implemented by a mobile device. The technique 700 may determine an amount of recovery time needed, based on a current fatigue level, so that the person can successfully complete the activity. As such, based on an expected time to recover from the current level, the person may be notified to rest (e.g., nap or sleep) for the particular duration. The technique 700 may include or may use a mapping from activity levels to expected exertion levels. Exertion levels may be or may be correlated with fatigue levels expected for the activity. Similarly or additionally, the mapping may include preferred recovery levels necessary for the activities. As such, the technique 700 can notify the user may indicate when the person should undertake the activity.

To illustrate, the person may indicate that they are excepting to drive for 10 hours starting at a particular time. The technique 700 can determine a current fatigue level, a amount of recovery required to undertake the task, and can recommend to the person to recover (e.g., sleep) at a particular time to sufficiently recover and/or undertake the activity at a time later than the time indicated by the person.

It may be appreciated that various changes can be made therein without departing from the spirit and scope of the disclosure. Moreover, the various features of the implementations described herein are not mutually exclusive. Rather any feature of any implementation described herein may be incorporated into any other suitable implementation.

Additional features may also be incorporated into the described systems and methods to improve their functionality. For example, those skilled in the art will recognize that the disclosure can be practiced with a variety of physiological monitoring devices, including but not limited to heart rate and blood pressure monitors, and that various sensor components may be employed. The devices may or may not comprise one or more features to ensure they are water resistant or waterproof. Some implementations of the devices may hermetically sealed.

Other implementations of the aforementioned systems and methods will be apparent to those skilled in the art from consideration of the specification and practice of this disclosure. It is intended that the specification and the aforementioned examples and implementations be considered as illustrative only, with the true scope and spirit of the disclosure being indicated by the following claims.

While the disclosure has been described in connection with certain implementations, it is to be understood that the disclosure is not to be limited to the disclosed implementations but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A method for fatigue evaluation based on sleep quality and physical activity using a wearable device, comprising:

continuously measuring, by an inward facing sensor of the wearable device facing toward or in contact with skin of a person, physiological data of the person while the wearable device is worn by the person, wherein the physiological data comprises heart rate data of the person continuously measured by the inward facing sensor;

determining, by a processor, a first sleep period and a second sleep period for the person based at least in part on the heart rate data of the person continuously measured by the inward facing sensor of the wearable device;

obtaining, by the processor, the heart rate data of a person measured during the first sleep period from the inward facing sensor;

determining, by the processor, a bathyphase time indicative of a minimum value of body temperature of the person during a day based at least in part on the heart rate data measured during the first sleep period;

determining, by the processor, a circadian rhythm (CR) oscillator for the person based at least in part on the bathyphase time, the CR oscillator indicating a predicted value of body temperature of the person at a particular time point of a day;

determining, by the processor, a sleep recovery of the second sleep period of the person based at least in part on the CR oscillator and at least one first sleep parameter determined from the physiological data measured during the second sleep period;

automatically updating, by the processor, a fatigue value for the person based on the sleep recovery of the second sleep period of the person;

in response to determining that the person is currently performing or about to perform an activity and that the updated fatigue value for the person is above a threshold, automatically determining, by the processor, a duration of recovery for the fatigue value of the person to decrease below the threshold based on the fatigue value; and outputting, on a user interface of the wearable device, an alert to the person for recommending the person to rest for the duration of recovery prior to performing the activity or continuing with the activity, wherein the method further comprises:

detecting a number of macro-movements over a time period;

when the number of macro-movements is above a threshold amount, turning off or not activating the at least one of the inward facing sensor or the second sensor for continuously measuring micro-movements; and activating the at least one of the inward facing sensor or the second sensor to continuously measure the micro-movements only when the number of macro-movements is below the threshold amount.

2. The method of claim 1, wherein determining the fatigue value for the person further comprises:

in response to determining that the person is not in sleep;

updating a total sleep inertia for the person based on a second time range indicative of wakefulness;

accumulating the fatigue value by a base physical fatigue factor, wherein the base physical fatigue factor is based on the heart rate data of the person; or determining the fatigue value based on the total sleep inertia for the person.

3. The method of claim 2, further comprising:

determining the base physical fatigue factor based on a determination that the person is performing a physical exercise from the physiological data.

4. The method of claim 1, further comprising:

determining, by the processor, a recovery debt for the person based on a previous fatigue value and a previous individual awakening period from a previous day from the physiological data, wherein the sleep recovery for the person is determined based on the recovery debt and the CR oscillator; or determining, by the processor, an initial bathyphase time for the person; and adjusting, by the processor, the initial bathyphase time based on historical heart rate data of the person to obtain adjusted bathyphase time, wherein the CR oscillator is determined based on at least one of the adjusted bathyphase time or a difference between the initial bathyphase time and the adjusted bathyphase time, and the CR oscillator for the person is determined based at least in part on the adjusted bathyphase time.

5. The method of claim 1, further comprising:

determining, by the processor, a total sleep recovery based on an accumulation of the sleep recovery during the sleep; and determining, by the processor, an adjusted total sleep recovery for the person based on a sleep quality of the person and the total sleep recovery, wherein the fatigue value is updated based on the adjusted total sleep recovery.

6. The method of claim 1, wherein the physiological data comprises the heart rate data of the person continuously measured by the inward facing sensor of the wearable device and motion data continuously obtained by the inward facing sensor or a second sensor of the wearable device, or the sleep quality is determined based on at least one of a number of awakenings during sleep or excess heart rate during the sleep from the physiological data.

7. The method of claim 1, further comprising:

determining an individual sleep need for the person based on at least one of characteristics information or the physiological data of the person; and in response to a determination that a sleep time duration is greater than the individual sleep need for the person, updating the fatigue value for the person based on the sleep time duration.

8. A non-transitory computer readable medium storing instructions operable to cause one or more processors to perform operations according to the method of claim 1.

9. The non-transitory computer readable medium of claim 8, wherein the operations further comprise at least one of:

in response to determining that the person is in sleep, accumulating, in a first time range indicative of the sleep, a total sleep inertia for the person based on at least one second sleep parameter obtained from the physiological data, and adjusting the fatigue value based on the total sleep inertia;

in response to determining that the person is not in sleep, updating the total sleep inertia for the person based on a second time range indicative of wakefulness; or determining a recovery debt for the person based on a previous fatigue value and a previous individual awakening period from a previous day from the physiological data, wherein the sleep recovery for the person is determined based on the recovery debt and the CR oscillator.

10. A device for fatigue evaluation of a person associated with the device, comprising:

an inward facing sensor facing toward or in contact with skin of the person and configured to obtain physiological data of the person, wherein the inward facing sensor comprises a heart rate sensor configured to continuously measure heart rate data of the person wearing the device, and the physiological data comprises the heart rate data of the person obtained by the inward facing sensor and motion data continuously measured by the inward facing sensor or a second sensor of the device;

a processor configured to execute instructions to:

obtain the physiological data of a person from the inward facing sensor, wherein a bathyphase time indicative of time-of-day of a minimum value of body temperature of the person is determined from the physiological data;

determine a circadian rhythm (CR) oscillator for the person based at least in part on the bathyphase time;

automatically determine a fatigue value for the person based on the CR oscillator, further comprising instructions to:

automatically determine whether the person is in sleep or not based on the physiological data wherein whether the person is in sleep or not is determined based at least in part on the heart rate data of the person obtained by the inward facing sensor and the motion data obtained by the inward facing sensor or the second sensor of the device;

in response to determining that the person is in sleep, update the fatigue value for the person based on a sleep recovery, wherein the sleep recovery is determined based on the CR oscillator and at least one first sleep parameter determined from the physiological data; and in response to determining that the person is currently performing or about to perform an activity and that the fatigue value for the person is above a threshold, determine a duration of recovery based on the fatigue value and generate an alert for the person to rest for the duration of recovery so as to decrease the fatigue value below the threshold prior to performing the activity or continuing with the activity;

detect a number of macro-movements over a time period;

when the number of macro-movements is above a threshold amount, turn off or not activate the at least one of the inward facing sensor or the second sensor for continuously measuring micro-movements; and activate the at least one of the inward facing sensor or the second sensor to continuously measure the micro-movements only when the number of macro-movements is below the threshold amount.

11. The device of claim 10, wherein the processor is further configured to:

in response to determining that the person is in sleep, accumulate, in a first time range indicative of the sleep, a total sleep inertia for the person based on at least one second sleep parameter obtained from the physiological data, and adjust the fatigue value based on the total sleep inertia; or in response to determining that the person is not in sleep, update the total sleep inertia for the person based on a second time range indicative of wakefulness.

12. The device of claim 11, wherein the instructions to calculate the fatigue value for the person further comprise instructions to:

in response to determining that the person is not in sleep, accumulate the fatigue value by a base physical fatigue factor, wherein the base physical fatigue factor is based on the heart rate data of the person; or in response to determining that the person is not in sleep, determine the fatigue value based on a total sleep inertia for the person determined from the physiological data.

13. The device of claim 10, wherein the processor is further configured to:

determine a recovery debt for the person based on a previous fatigue value and a previous individual awakening period from a previous day from the physiological data, wherein the sleep recovery for the person is determined based on the recovery debt and the CR oscillator.

14. The device of claim 10, wherein the processor is further configured to:

determining a total sleep recovery based on an accumulation of the sleep recovery during the sleep; and determining an adjusted total sleep recovery for the person based on a sleep quality of the person and the total sleep recovery, wherein the fatigue value is updated based on the adjusted total sleep recovery.

15. The device of claim 14, wherein the physiological data comprises heart rate data of the person obtained by the inward facing sensor of the device and motion data obtained by the inward facing sensor or a second sensor of the device, or the sleep quality is determined based on at least one of a number of awakenings during sleep or excess heart rate during the sleep from the physiological data.

16. The device of claim 10, wherein the processor is further configured to:

determine an individual sleep need for the person based on at least one of characteristics information or the physiological data of the person; and in response to a determination that a sleep time duration is greater than the individual sleep need for the person, update the fatigue value for the person based on the sleep time duration.

17. A method for fatigue evaluation based on sleep quality and physical activity using a wearable device, comprising:

continuously measuring physiological data of a person while the wearable device is worn by the person, wherein the physiological data comprises heart rate data of the person continuously measured by an inward facing sensor of the wearable device facing toward or in contact with skin of the person, and motion data comprising micro-movement data of the person continuously measured by the inward facing sensor or a second sensor of the wearable device;

determining, by a processor, a bathyphase time indicative of time-of-day of a minimum value of body temperature of the person from the physiological data, and a circadian rhythm (CR) oscillator for the person based at least in part on the bathyphase time;

automatically determining, by the processor, a fatigue value for the person based on the CR oscillator, further comprising:

automatically determining at least one sleep period of the person based at least in part from the heart rate data of the person continuously measured by the inward facing sensor of the wearable device;

automatically detecting, by the inward facing sensor or the second sensor of the wearable device, a number of macro-movements over a time period;

when the number of macro-movements is above a threshold amount, automatically turning off or not activating, by the processor, the at least one of the inward facing sensor or the second sensor for continuously measuring the micro-movements; and automatically activating the at least one of the inward facing sensor or the second sensor to continuously measure the micro-movements only when the number of macro-movements is below the threshold amount;

in response to determining the at least one sleep period of the person, updating, by the processor, the fatigue value for the person based on a sleep recovery, wherein the sleep recovery is determined based on the CR oscillator and at least one first sleep parameter determined from the physiological data; and in response to determining that the person is currently performing or about to perform an activity and that the fatigue value for the person is above a threshold, automatically determining, by the processor, a duration of recovery based on the fatigue value and automatically generating, by the processor, an alert on the wearable device, the alert comprising the duration of recovery, and a recommendation to the person to rest for the duration of recovery so as to decrease the fatigue value below the threshold prior to performing the activity or continuing with the activity.

18. The method of claim 17, further comprising:

determining, by the processor, a total sleep recovery based on an accumulation of the sleep recovery during the sleep; and determining, by the processor, an adjusted total sleep recovery for the person based on a sleep quality of the person and the total sleep recovery, wherein the fatigue value is updated based on the adjusted total sleep recovery.

19. The method of claim 17, further comprising:

determining, by the processor, a recovery debt for the person based on a previous fatigue value and a previous individual awakening period from a previous day from the physiological data, wherein the sleep recovery for the person is determined based on the recovery debt and the CR oscillator; or determining, by the processor, an initial bathyphase time for the person; and adjusting, by the processor, the initial bathyphase time based on historical heart rate data of the person to obtain adjusted bathyphase time, wherein the CR oscillator is determined based on at least one of the adjusted bathyphase time or a difference between the initial bathyphase time and the adjusted bathyphase time, and the CR oscillator for the person is determined based at least in part on the adjusted bathyphase time.

20. The method of claim 17, further comprising:

determining an individual sleep need for the person based on at least one of characteristics information or the physiological data of the person; and in response to a determination that a sleep time duration is greater than the individual sleep need for the person, updating the fatigue value for the person based on the sleep time duration.

* * * * *